(12) United States Patent
Mantegani et al.

(10) Patent No.: US 6,765,003 B1
(45) Date of Patent: Jul. 20, 2004

(54) 3-ARYLSULFONYL-2 (SUBSTITUTED METHYL) PROPANOIC ACID DERIVATIVES AS MATRIX METALLOPROTEINASE INHIBITORS

(75) Inventors: Sergio Mantegani, Milan (IT); Francesca Abrate, Milan (IT); Pierluigi Bissolino, Pavia (IT); Paolo Cremonesi, Milan (IT); Ettore Perrone, Milan (IT); Daniela Jabes, Milan (IT)

(73) Assignee: Pharmacia Italia, SpA, Milan (IT)

( * ) Notice: Subject to any disclaimer, the term of this patent is extended or adjusted under 35 U.S.C. 154(b) by 98 days.

(21) Appl. No.: 10/030,681

(22) PCT Filed: Jul. 7, 2000

(86) PCT No.: PCT/EP00/06429

§ 371 (c)(1),
(2), (4) Date: Apr. 9, 2002

(87) PCT Pub. No.: WO01/05756

PCT Pub. Date: Jan. 25, 2001

(30) Foreign Application Priority Data

Jul. 14, 1999 (GB) ................................................ 9916562

(51) Int. Cl.$^7$ .................... A61K 31/33; A61K 31/4164; C07D 233/40; C07D 233/00
(52) U.S. Cl. ...................... 514/183; 514/389; 514/390; 514/425; 548/300.1; 548/316.4; 548/317.1
(58) Field of Search ................................ 514/183, 389, 514/390, 425; 548/300.1, 316, 317.1

(56) References Cited

FOREIGN PATENT DOCUMENTS

| WO | 98 05635 | | 2/1998 |
| WO | 98 13340 | | 4/1998 |
| WO | 9813340 | * | 4/1998 |

OTHER PUBLICATIONS

Chemical Abstract DN 128:270437.*

* cited by examiner

Primary Examiner—Richard L. Raymond
Assistant Examiner—Sudhaker B. Patel
(74) Attorney, Agent, or Firm—Akin Gump Strauss Hauer & Feld LLP; Dwayne L. Mason

(57) ABSTRACT

Compounds which are 3-arylsulfonyl-2-methyl propanoic acid derivatives of formula (I): wherein X is HO—NH— or HO—, R1 is selected from phenyl, 4-chlorophenyl, 4-florophenyl, 4-cyanophenyl, benzamido (i.e., —NH—CO-Ph) and benzamido substituted on the terminal phenyl ring by $C_1$–$C_4$ alkyl, fluoro, chloro, cyano or $C_{1-4}$ alkoxy; $R_2$ is selected from (a) —S—Ar or —S—$CH_2$—Ar wherein Ar is an aromatic moiety; (b) —O—Ar wherein Ar is as defined above; (c) —S-Het or —S—$CH_2$-Het wherein Het is a heterocyclic ring; and (d) 2,5-dioxo-1-imidazolidinyl or 2,4-dioxo-1-imidazolinyl; and the pharmaceutically acceptable salts thereof; have potent and selective inhibitory activity against matrix metalloproteinases (MMPs) and can thus be used in the treatment and prevention of diseases mediated by MMPs.

13 Claims, No Drawings

3-ARYLSULFONYL-2 (SUBSTITUTED METHYL) PROPANOIC ACID DERIVATIVES AS MATRIX METALLOPROTEINASE INHIBITORS

FIELD OF THE INVENTION

The present invention relates to some O-sulfonyl hydroxamic and carboxylic acids displaying potent and selective inhibitory activity against some Matrix MetalloProteinases (MMPs), to their use for the treatment of diseases in which the proteolytic activity of these MMPs is involved, to methods for their preparation, and to pharmaceutical compositions containing them.

BACKGROUND OF THE INVENTION

Under physiological conditions MMPs play an important role in normal tissue turnover and development. However, increased MMP activity and/or impairment of the physiological MMP inhibitors has been associated with a variety of pathological conditions such as cancer, rheumatoid arthritis, osteoarthritis, osteoporosis, multiple sclerosis, stroke, arteriosclerosis, restenosis and age-related macular degeneration. In cancer, the contribution of MMPs is manifold and not limited to destruction of the extracellular matrix required for local and distal invasion. The proteolytic action of MMPs generates active matrix protein fragments, and influence the release, activation and bioavailability of growth factors. In addition, MMPs are involved in cell migration and in the processing or shedding of cell surface proteins. It is now believed that the proteolytic action of MMPs plays a very important role in tumor growth, apoptosis and angiogenesis (see Noel, A. et al., 'Emerging Roles for Proteinases in Cancer', Invasion Metastasis 17:221–239, 1997). Among the several MMPs known to date, gelatinase-A (MMP-2) is currently reputed as the main target in cancer.

Potent MMP inhibitors (MMPIs) were disclosed three decades ago (e.g., see Dickens, J. P. et al., U.S. Pat. No. 4,599,361), but only recently some of them entered clinical trials, and none has arrived at the market yet. Questions remain concerning their specificity, bioavailability, and potential long-tens toxicity (see Hodgson, J., 'Remodeling MMPIs', Biotechnology 13:554–557, 1995), especially because they are primarily intended (in arthritis and cancer, at least) for prolonged therapy. Marimastat, the most advanced MMPI in the clinic, and other compounds currently investigated in patients such as Novartis CGS27023A and Agouron AG3340, have been reported to cause a musculoskeletal syndrome characterized by joint pain and stiffness, which may be severe and dose-limiting. Although the cause of this toxicity is not well understood at this moment, it is thought to arise from an impairment in the normal tissue remodeling that is governed by one or more of the MMPs, primarily fibroblast collagenase (MMP-1). We have extended these observations by developing an animal model of joint toxicity, involving treatment of rats for 10 days with MMPIs at exposures close to that required for antitumor efficacy in mice (human prostate DU-145 model). In this rat model, MMPIs characterized by poor selectivity (i.e., comparable potency against MMP-2 and MMP-1), such as marimastat and Roche Ro31-9790, elicited histological alteration of stifle joints (hypertrophic fibrosis of ligaments, interstitial hypertrophic fibrosis of skeletal muscles, hypertrophic fibroplasia of the periostium and synovium, chondrodysplasia, and decreased endochondrial ossification of the ephyseal plate); in some cases, clinical symptoms (abnormal posture, reluctance to move, abnormal gait) were also observed. Thus, there is a strong need for better MMPIs, especially as far as the properties referred to above (specificity, bioavailability, long-term toxicity) are concerned. The compounds of the present invention are intended to provide these advantages.

INFORMATION DISCLOSURE

A previous disclosure by the Pharmacia & Upjohn Company, PCT Patent Application WO 98/13340 (U.S. Pat. No. 5,847,153), provides a broad range of β-sulfonyl hydroxamic acid derivatives, their preparation, and their activity against various enzymes of the MMP family, predominantly stromelysin and gelatinase. These compounds are generically described by the formula (Ia):

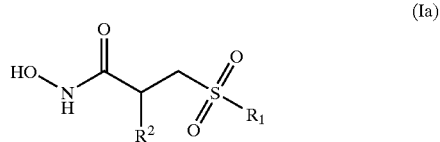

(Ia)

wherein $R_1$ is $C_{4-12}$ alkyl, $C_{4-12}$ alkenyl, $C_{4-12}$ alkynyl, —$(CH_2)_n$—$C_{3-8}$ cycloalkyl, —$(CH_2)_n$-aryl, or —$(CH_2)_n$-het; $R_2$ is $C_{1-12}$ alkyl, $C_{2-12}$ alkenyl, $C_{2-12}$ alkynyl, —$(CH_2)_n$—$C_{3-8}$ cycloalkyl, —$(CH_2)_n$—$C_{3-8}$ cycloalkenyl, —$(CH_2)_n$-aryl, —$(CH_2)_n$-het, —$(CH_2)_n$—Q, —$(CH_2)_r$—X—$R_4$, or —$(CH_2)_r$—$CHR_5R_6$.

We have now found that the combination of few particular groups $R_1$ and $R_2$ in a molecule of formula (Ia) provides distinct advantages over the other compounds of this class of MMPIs. Said combination, which is an object of the present invention, is associated with outstanding potency (Ki in the picomolar range) against the gelatinases, in particular MMP-2, and relatively weak activity against fibroblast collagenase (MMP-1). Further, we have found that the same combination confers good potency (low nanoM range) and even higher selectivity for MMP-2 to the corresponding carboxylates, which were previously described as intermediates but not claimed as such. Finally, we have found that the same combination provides advantages in the pharmacokinetic parameters, in particular lower clearance and higher oral bioavailability, and that antitumor efficacy in rodents can be achieved in the absence of joint toxicity.

DESCRIPTION OF THE INVENTION

The present invention provides 3-arylsulfonyl-2-methyl propanoic acid derivatives of formula (I):

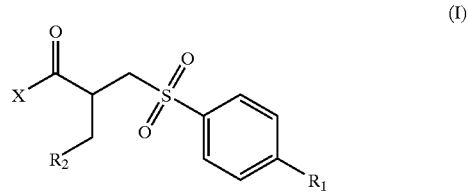

(I)

or pharmaceutically acceptable salts thereof wherein:
  X is either HO—NH— (hydroxamic acids) or HO— (carboxylic acids);
  $R_1$ is selected from phenyl, 4-chlorophenyl, 4-fluorophenyl, 4-cyanophenyl, benzamido (i.e., —NH—CO—Ph) or benzamido substituted on the terminal Ph ring by $C_{1-4}$ alkyl, fluoro, chloro, cyano, $C_{1-4}$ alkoxy;

$R_2$ is selected from:

(a) —S—Ar or —S—CH$_2$—Ar, wherein Ar is a monocarbocyclic or bicarbocyclic aromatic moiety, preferably phenyl, naphthyl and biphenyl, which is either unsubstituted or substituted with one or two substituents selected from the group consisting of C$_{1-4}$ alkyl, phenyl, benzyl, C$_{1-4}$ alkoxy, fluoro, chloro, bromo, nitro, cyano, hydroxy, amino, dimethylamino, acetamido, methylthio and acetyl;

(b) O—Ar, wherein Ar is as defined above;

(c) —S-Het or —S—CH$_2$-Het, wherein Het is a heterocyclic ring selected from the group consisting of pyridine, pyrimidine, pyridazine, pyrazine, 1,2,5-triazine, imidazole, thiophene, furan, pyrrole, pyrazole, 1,3-thiazole, 1,3-oxazole, 1,2,3-triazole, 1,2,4-triazole, 1,3,4-thiadiazole, 1,3,4-oxadiazole, 1,2,3,4-tetrazole, quinoline, isoquinoline, indole, 1,3-benzoxazole, 1,3-benzothiazole, benzimidazole, [1,3]oxazolo[4,5-b]pyridine, [1,3]thiazolo[4,5-b]pyridine, [1,2,3,4]tetrazolo[1,5-b]pyridazine and purine, and wherein said Het group can be substituted with one to three substituents selected from the group consisting of C$_{1-4}$ alkyl, phenyl, pyridyl, benzyl, C$_{1-4}$ alkoxy, methylthio, fluoro, chloro, nitro, cyano, hydroxy, oxo, amino, methylamino, dimethylamino, 2-dimethylaminoethyl, acetamido and acetyl;

(d) 2,5-dioxo-1-imidazolidinyl or 2,4-dioxo-1-imidazolidinyl, which can be substituted at the carbon atom with one or two methyl groups, or with C$_{2-4}$ linear or branched alkyl, phenyl, benzyl or hydroxymethyl, and at the nitrogen atom with C$_{1-4}$ linear or branched alkyl.

The compounds of the present invention can be converted to pharmaceutically acceptable salts, where appropriate, according to conventional methods. The term 'pharmaceutically acceptable salts' refers to acid addition salts useful for administering the compounds of this invention and includes hydrochloride, sulfate, phosphate, acetate, propionate, lactate, mesylate, maleate, malate, succinate, tartrate, citrate, 2-hydroxyethyl sulfonate, fumarate and the like. Alternatively, the compounds of this invention, especially when X in formula (I) is hydroxy, may form metal salts, such as sodium, potassium, calcium or magnesium, or ammonium salts, or salts with an appropriate organic amine or amino acid such as arginine, procaine and the like. Any salt may be either in the anhydrous or hydrated form, or may be solvated with acceptable solvents, such as ethanol.

The present invention also provides pharmaceutical compositions which comprise, as active ingredient, a compound of formula (I) or a solvate, hydrate, or pharmaceutically acceptable salt thereof, and a pharmaceutically acceptable carrier, diluent or excipient.

The compounds of this invention contain a chiral center at the α-position of the hydroxamic or carboxylic acid, and as such they may be obtained as any of the two separate enantiomers or as a racemic mixture of both. Preferred compounds of this invention are either the racemates or individual isomers having the configuration depicted in the formula (I') herebelow:

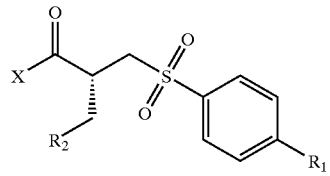

(I')

wherein X, $R_1$ and $R_2$ are as defined above. According to the Cahn-Ingold-Prelog rule, these preferred isomer are denoted as (R) when $R_2$ is O—Ar, 2,5-dioxoimidazolidin-1-yl or 2,4-dioxoimidazolidin-1-yl, and as (S) when $R_2$ is —S—Ar, S-Het, —S—CH$_2$—Ar or —S—CH$_2$-Het. In addition, depending on the substituents, additional chiral centers or other isomeric forms may be present, and this invention embraces all possible stereoisomers and geometrical forms.

Particularly preferred compounds of this invention are as follows:

3-[(4'-Chloro[1,1'-biphenyl]-4-yl)sulfonyl]-2-[(phenylsulfanyl)methyl]propanoic acid;

(2S)-3-[(4'-Chloro[1,1'-biphenyl]-4-yl)sulfonyl]-2-[(phenylsulfanyl)methyl]propanoic acid;

3-[(4'-Chloro[1,1'-biphenyl]-4-yl)sulfonyl]-N-hydroxy-2-[(phenylsulfanyl)methyl]-propanamide;

3-[(4'-Chloro[1,1'-biphenyl]yl)sulfonyl]-2-[[(4-hydroxyphenyl)sulfanyl]methyl]propanoic acid;

3-[(4'-Chloro[1,1'-biphenyl]-4-yl)sulfonyl]-N-hydroxy-2-[[(4-hydroxyphenyl)sulfanyl]-methyl]propanamide;

3-[(4'-Chloro[1,1'-biphenyl]-4-yl)sulfonyl]-2-(phenoxymethyl)propanoic acid;

3-[(4'-Chloro[1,1'-biphenyl]-4-yl)sulfonyl]-N-hydroxy-2-(phenoxymethyl)propanamide;

3-[(4'-Chloro[1,1'-biphenyl]-4-yl)sulfonyl]-2-[(2-pyridinylsulfanyl)methyl]propanoic acid;

3-[(4'-Chloro[1,1'-biphenyl]-4-yl)sulfonyl]-N-hydroxy-2-[(2-pyridinylsulfanyl)methyl]-propanamide;

3-[(4'-Chloro[1,1'-biphenyl]-4-yl)sulfonyl]-2-[[(2-pyridinylmethyl)sulfanyl]methyl]-propanoic acid;

3-[(4'-Chloro[1,1'-biphenyl]-4-yl)sulfonyl]-N-hydroxy-2-[[(2-pyridinylmethyl)sulfanyl]methyl]propanamide;

3-[(4'-Chloro[1,1'-biphenyl]-4-yl)sulfonyl]-2-[[(5-methyl-1,3,4-thiadiazol-2-yl)sulfanyl]-methyl]propanoic acid;

3-[(4'-Chloro[1,1'-biphenyl]-4-yl)sulfonyl]-N-hydroxy-2-[[(5-methyl-1,3,4-thiadiazol-2-yl)sulfanyl]methyl]propanamide;

3-[(4'-Chloro[1,1'-biphenyl]-4-yl)sulfonyl]-2-[[(5-amino-1,3,4-thiadiazol-2-yl)-sulfanyl]-methyl]propanoic acid;

3-[(4'-Chloro[1,1'-biphenyl]-4-yl)sulfonyl]-2-[[(1-methyl-1H-imidazol-2-yl)sulfanyl]methyl]propanoic acid;

3-[(4'-Chloro[1,1'-biphenyl]-4-yl)sulfonyl]-2-[(2-pyrimidinylsulfanyl)methyl]propanoic acid;

3-[(4'-Chloro[1,1'-biphenyl]-4-yl)sulfonyl]-2-[[(1-methyl-1H-tetrazol-5-yl)sulfanyl]methyl]propanoic acid;

3-[(4'-Chloro[1,1'-biphenyl]-4-yl)sulfonyl]-2-[[(1-benzyl-1H-tetrazol-5-yl)sulfanyl]methyl]propanoic acid;

3-[(4'-Chloro[1,1'-biphenyl]-4-yl)sulfonyl]-2-[(1H-benzimidazol-2-ylsulfanyl)methyl]propanoic acid;

3-[(4'-Chloro[1,1'-biphenyl]-4-yl)sulfonyl]-2-[(1,3-thiazol-2-ylsulfanyl)methyl]propanoic acid;

3-[(4'-Chloro[1,1'-biphenyl]-4-yl)sulfonyl]-2-[[(2-methyl-2H-1,2,3-triazol-4-yl)sulfanyl]-methyl]propanoic acid;

3-[(4'-Chloro[1,1'-biphenyl]-4-yl)sulfonyl]-2-[[(5-phenyl-1,3,4-oxadiazol-2-yl)sulfanyl]-methyl]propanoic acid;

3-[(4'-Chloro[1,1'-biphenyl]-4-yl)sulfonyl]-2-[[[1-(3-pyridinyl)-1H-imidazol-2-yl]sulfanyl]methyl]propanoic acid;

3-[(4'-Chloro[1,1'-biphenyl]-4-yl)sulfonyl]-2-[[(4-methyl-1,3-oxazol-2-yl)sulfanyl]methyl]propanoic acid;

3-[(4'-Chloro[1,1'-biphenyl]-4-yl)sulfonyl]-2-[([1,3]oxazolo[4,5-b]pyrimidin-2-yl-sulfanyl)methyl]propanoic id;

3-[(4'-Chloro[1,1'-biphenyl]-4-yl)sulfonyl]-2-[([1,2,3,4]tetrazolo[1,5-b]pyridazin-6-yl-sulfanyl)methyl]propanoic acid;

3-[(4'-Chloro[1,1'-biphenyl]-4-yl)sulfonyl]-2-[[(2,6-dimethylpyrimidinyl)sulfanyl]-methyl]propanoic acid;

3-[(4'-Chloro[1,1'-biphenyl]-4-yl)sulfonyl]-2-[[(4,6-dimethyl-2-pyrimidinyl)sulfanyl]methyl]propanoic acid;

3-[(4'-Chloro[1,1'-biphenyl]-4-yl)sulfonyl]-2-[[(4-hydroxy-6-methyl-2-pyrimidinyl)sulfanyl]methyl]propanoic acid;

3-[(4'-Chloro[1,1'-biphenyl]-4-yl)sulfonyl]-2-[[(4,6-dihydroxy-2-pyrimidinyl)sulfanyl]methyl]propanoic acid;

3-[(4'-Chloro[1,1'-biphenyl]-4-yl)sulfonyl]-2-[(9H-pufin-6-ylsulfanyl)methyl]propanoic acid;

3-[(4'-Chloro[1,1'-biphenyl]-4-yl)sulfonyl]-2-(3-fluorophenoxymethyl)propanoic acid;

3-[(4'-Chloro[1,1'-biphenyl]-4-yl)sulfonyl]-2-[(2-acetylaminophenoxy)methyl]propanoic acid;

3-[(4'-Chloro[1,1'-biphenyl]-4-yl)sulfonyl]-2-[(4-acetylaminophenoxy)methyl]propanoic acid;

3-([1,1'-Biphenyl]-4-ylsulfonyl)-2-[(3,4,4-trimethyl-2,5-dioxo-1-imidazolidinyl)methyl]-propanoic acid;

3-[(4'-Chloro[1,1'-biphenyl]-4-yl)sulfonyl]-2-[(3,4,4-trimethyl-2,5-dioxo-1-imidazolidinyl)methyl]propanoic acid;

(2R)-3-[(4'-Chloro[1,1'-biphenyl]-4-yl)sulfonyl]-2-[(3,4,4-trimethyl-2,5-dioxo-1-imidazolidinyl)methyl]propanoic acid;

3-[(4'-Chloro[1,1'-biphenyl]-4-yl)sulfonyl]-N-hydroxy-2-[(3,4,4-trimethyl-2,5-dioxo-1-imidazolidinyl)methyl]propanamide;

3-[(4'-Chloro[1,1'-biphenyl]-4-yl)sulfonyl]-2-[(4,4-dimethyl-2,5-dioxo-1-imidazolidinyl)methyl]propanoic acid;

3-[(4'-Chloro[1,1'-biphenyl]-4-yl)sulfonyl]-N-hydroxy-2-[(4,4-dimethyl-2,5-dioxo-1-imidazolidinyl)methyl]propanamide;

3-[(4'-Chloro[1,1'-biphenyl]-4-yl)sulfonyl]-2-[(2,5-dioxo-1-imidazolidinyl)methyl]propanoic acid;

3-[(4'-Chloro[1,1'-biphenyl]-4-yl)sulfonyl]-N-hydroxy-2-[(2,5-dioxo-1-imidazolidinyl)methyl]propanamide;

3-[(4'-Chloro[1,1'-biphenyl]-4-yl)sulfonyl]-2-[(3-methyl-2,5-dioxo-1-imidazolidinyl)methyl]propanoic acid;

3-[(4'-Chloro[1,1'-biphenyl]-4-yl)sulfonyl]-2-[(3-ethyl-2,5-dioxo-1-imidazolidinyl)methyl]propanoic acid;

3-[(4'-Chloro[1,1'-biphenyl]-4-ylsulfonyl]-2-[(3-butyl-2,5-dioxo-1-imidazolidinyl)methyl]propanoic acid;

3-[(4'-Chloro[1,1'-biphenyl]-4-yl)sulfonyl]-N-hydroxy-2-[(3-butyl-2,5-dioxo-1-imidazolidinyl)methyl]propanamide;

3-[(4'-Chloro[1,1'-biphenyl]-4-yl)sulfonyl]-2-[(3-butyl-2,4-dioxo-1-imidazolidinyl)methyl]propanoic acid;

3-[(4'-Chloro[1,1'-biphenyl]-4-yl)sulfonyl]-N-hydroxy-2-[(3-butyl-2,4-dioxo-1-imidazolidinyl)methyl]propanamide;

3-[(4'-Chloro[1,1'-biphenyl]-4-yl)sulfonyl]-2-[(5-isopropyl-2,4-dioxo-1-imidazolidinyl)methyl]propanoic acid;

3-[(4'-Chloro[1,1'-biphenyl]-4-yl)sulfonyl]-2-[(5-hydroxymethyl-2,4-dioxo-1-imidazolidinyl)methyl]propanoic acid;

3-[(4'-Chloro[1,1'-biphenyl]-4-yl)sulfonyl]-2-[(5-hydroxymethyl-3-methyl-2,4-dioxo-1-imidazolidinyl)methyl]propanoic acid;

3-[(4'-Fluoro[1,1'-biphenyl]-4-yl)sulfonyl]-2-[(phenylsulfanyl)methyl]propanoic acid;

3-[(4'-Fluoro[1,1'-biphenyl]-4-yl)sulfonyl]-N-hydroxy-2-[(phenylsulfanyl)methyl]propanamide;

3-[(4'-Fluoro[1,1'-biphenyl]-4-yl)sulfonyl]-2-(phenoxymethyl)propanoic acid;

3-[(4'-Fluoro[1,1'-biphenyl]-4-yl)sulfonyl]-N-hydroxy-2-(phenoxymethyl)propanamide;

3-[(4'-Cyano[1,1'-biphenyl]-4-yl)sulfonyl]-2-[(phenylsulfanyl)methyl]propanoic acid;

3-[(4'-Cyano[1,1'-biphenyl]-4-yl)sulfonyl]-N-hydroxy-2-[(phenylsulfanyl)methyl]propanamide;

3-[(4'-Cyano[1,1'-biphenyl]-4-yl)sulfonyl]-2-(phenoxymethyl)propanoic acid;

3-[(4'-Cyano[1,1'-biphenyl]-4-yl)sulfonyl]-N-hydroxy-2-phenoxymethyl)propanamide;

3-[(4'-Cyano[1,1'-biphenyl]-4-yl)sulfonyl]-2-(3-fluorophenoxymethyl)propanoic acid;

3-[(4'-Cyano[1,1'-biphenyl]-4-yl)sulfonyl]-2-[(2-acetylamino)phenoxymethyl]propanoic acid;

3-[(4'-Cyano[1,1'-biphenyl]-4-yl)sulfonyl]-2-[(2-pyridinylsulfanyl)methyl]propanoic acid;

3-[(4'-Cyano[1,1'-biphenyl]-4-yl)sulfonyl]-2-[[(2-pyridinylmethyl)sulfanyl]methyl]propanoic acid;

3-[(4'-Cyano[1,1'-biphenyl]-4-yl)sulfonyl]-2-[(3-butyl-2,5-dioxo-1-imidazolidinyl)methyl]propanoic acid;

3-[(4'-Cyano[1,1'-biphenyl]-4-yl)sulfonyl]-N-hydroxy-2-[(3-butyl-2,5-dioxo-1-imidazolidinyl)methyl]propanamide;

3-[(4'-Cyano[1,1'-biphenyl]-4-yl)sulfonyl]-2-[(5-hydroxymethyl-2,4-dioxo-1-imidazolidinyl)methyl]propanoic acid;

3-[[4-(Benzoylamino)phenyl]sulfonyl]-2-[(phenylsulfanyl)methyl]propanoic acid;

3-[[4-(Benzoylamino)phenyl]sulfonyl]-N-hydroxy-2-[(phenylsulfanyl)methyl]propanamide;

3-[[4-(Benzoylamino)phenyl]sulfonyl]-2-[[(2-pyridinylmethyl)sulfanyl]methyl]propanoic acid;

3-[[4-(Benzoylamino)phenyl]sulfonyl]-2-[(2-thienylsulfanyl)methyl]propanoic acid;

3-[[4-(Benzoylamino)phenyl]sulfonyl]-2-(phenoxymethyl)propanoic acid;

3-[[4-[(4-Methylbenzoyl)amino]phenyl]sulfonyl]-2-[(phenylsulfanyl)methyl]propanoic acid;

3-[[4-[(4-Methylbenzoyl)amino]phenylsulfonyl]-N-hydroxy-2-[(-phenylsulfanyl)methyl]propanamide;

3-[[4-[(4-Chlorobenzoyl)amino]phenyl]sulfonyl]-2-[(phenylsulfanyl)methyl]propanoic acid;

3-[[4-[(4-Chlorobenzoyl)amino]phenyl]sulfonyl]-N-hydroxy-2-[(phenylsulfanyl)methyl]propanamide;

3-[[4-[(4-Chlorobenzoyl)amino]phenyl]sulfonyl]-2-(phenoxymethyl)propanoic acid;

3-[[4-[(4-Chlorobenzoyl)amino]phenyl]sulfonyl]-N-hydroxy-2-(phenoxymethyl)propanamide;

3-[[4-[(4-Clorobenzoyl)amino]phenyl]sulfonyl]-2-(3-fluorophenoxymethyl)propanoic acid;

3-[[4-[(4-Chlorobenzoyl)amino]phenyl]sulfonyl]-2-[[(2-pyridinylmethyl)sulfanyl]methyl]propanoic acid;

3-[[4-[(4-Chlorobenzoyl)amino]phenyl]sulfonyl]-2-[[(1-methyl-1H-tetrazol-5-yl)sulfanyl]methyl]propanoic acid;

3-[[4-[(4-Chlorobenzoyl)amino]phenyl]sulfonyl]-2-[(5-hydroxymethyl-2,4-dioxo-1-imidazolidinyl)methyl] propanoic acid;

3-[[4-[(4-Cyanobenzoyl)amino]phenyl]sulfonyl]-2-[(phenylsulfanyl)methyl]propanoic acid;

3-[[4-[(4-Cyanobenzoyl)amino]phenyl]sulfonyl]-N-hydroxy-2-[(phenylsulfanyl)methyl]propanamide;

3-[[4-[(4-Cyanobenzoyl)amino]phenyl]sulfonyl]-2-[[(1-methyl-1H-tetrazol-5-yl)sulfanyl]methyl]propanoic acid;

3-[[4-[(4-Cyanobenzoyl)amino]phenyl]sulfonyl]-2-(phenoxymethyl)propanoic acid;

3-[[4-[(4-Cyanobenzoyl)amino]phenyl]sulfonyl]-N-hydroxy-2-(phenoxymethyl)propanamide;

3-[4-[(4-Cyanobenzoyl)amino]phenyl]sulfonyl]-2-(3-fluorophenoxymethyl)propanoic acid;

3-[[4-[(4-Cyanobenzoyl)amino]phenyl]sulfonyl]-N-hydroxy-2-(3-fluorophenoxymethyl)propanamide;

3-[[4-[(4-Cyanobenzoyl)amino]phenyl]sulfonyl]-2-[(2-acetylamino)phenoxymethyl]propanoic acid;

3-[[4-(4-Propylbenzoylamino)phenyl]sulfonyl]-2-[[(1-methyl-1H-tetrazol-5-yl)sulfanyl]methyl]propanoic acid;

3-[[4-[(4-Methoxybenzoyl)amino]phenyl]sulfonyl]-2-(phenoxymethyl)propanoic acid;

3-[(4'-Chloro[1,1'-biphenyl]-4-yl)sulfonyl]-2-[[2-(hydroxymethyl)phenoxy]methyl]propanoic acid.

The compounds of this invention can be prepared by a process starting from a compound of formula 4:

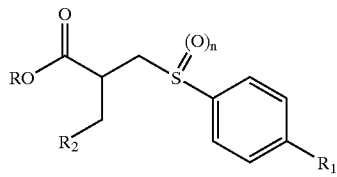

(4)

wherein R is H or the residue of a carboxylic acid ester, $R_1$ and $R_2$ are as defined above and n is 0 or 2, which process comprises:

(a) hydrolysing a said compound of formula 4 in which R is the residue of a carboxylic and ester to give a compound of formula (I) in which X is HO—; or (b) hydrolysing and oxidising, in either order, a said compound of formula 4 in which n is 0 and R is the residue of a carboxylic acid ester, to give a compound of formula (I) in which X is HO—; or (c) activating a said compound of formula 4 wherein R is H and n is 2 to form an activated carboxy group, coupling the activated carboxy group with hydroxylamine or an O-protected derivative thereof and, if necessary, deprotecting the hydroxamic group to give a compound of formula (I) wherein X is —NHOH; or (d) submitting a said compound of formula 4 wherein R is H and n is zero to a sequence of reactions comprising oxidation at the sulphur atom, activation of the carboxy group, condensation of the activated carboxy group with hydroxylamine or an O-protected derivative thereof and, if necessary, deprotection of the hydroxamic group to form a compound of formula (I) wherein X is —NHOH, the oxidation step being conducted either before the activation step or after the condensation step; and/or (e) if desired, converting a resulting compound of formula (I) into another compound of formula (I); and/or converting a free compound into a pharmaceutically acceptable salt thereof; and/or converting a salt into a free compound.

The compound of formula 4 may be obtained by (a) subjecting a compound of formula 2:

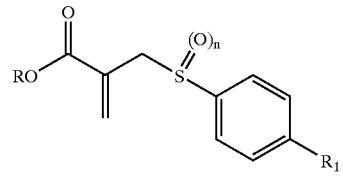

(2)

wherein R, $R_1$ and n are as defined above, to conjugate addition by treatment with a compound of formula $R_2H$ wherein $R_2$ is as defined above; or (b) treating a compound of formula 3:

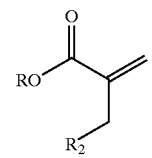

(3)

wherein R and $R_2$ are as defined above, with a thiol of formula:

to obtain a compound of formula 4 in which n is zero.

These processes are depicted in the following Scheme 1, where $R_1$ and $R_2$ are the groups as defined previously, R is either a hydrogen atom or the residue of a carboxylic ester such as methyl, ethyl, n-butyl, tert-butyl, benzyl or benzhydryl, and n is either zero or 2. Compound 1, i.e. 2-(bromomethyl)acrylic acid or an ester thereof, is reacted with the appropriate aryl-thiol in a suitable solvent such as toluene or dimethylformamide (DMF) in the absence or presence of a suitable base such as sodium bicarbonate or triethylamine TEA), at ambient temperature or under heating up to reflux temperature, to afford a compound 2 wherein n is zero. The corresponding sulfone (i.e., a compound 2 wherein n is 2) is obtained, if desired, by subsequent reaction with an oxidant such as metachloroperbenzoic acid (MCPBA) in a suitable solvent such as dichloromethane (DCM) at 0° C. or ambient temperature, or using hydrogen peroxide in acidic acid; preferably, this reaction is performed with potassium peroxymonosulfate (Oxone®) in an organic solvent, preferably DMF, or in a mixture of water and water-miscible organic solvents such as methanol, DMF or the combination of two, at ambient temperature or under moderate heating. Alternatively, a compound 2 wherein n is 2 can be obtained from compound 1 directly, by reaction with the appropriate arylsulfinate. Preferably, the sulfinate is obtained and used as the sodium salt, or as the salt with a tertiary organic amine such as N-methylmorpholine (NMM). The sodium arylsulfinate can be conveniently obtained by reaction of the appropriate aryl-sulfonyl chloride with sodium iodide in acetone, preferably at ambient temperature, and it is isolated before reaction with compound 1, which takes place in a suitable solvent such as toluene in the absence or presence of a suitable base such as sodium bicarbonate, at a temperature ranging from 25° C. to reflux. The salt with NMM is obtained by reaction of the arylsulfonyl chloride with 4-thiocresol and NMM in DCM, preferably at a temperature ranging from −50 to −78° C., and it is reacted in situ with compound 1, then raising the temperature up to 25° C. or reflux.

A compound 4 can be obtained from the corresponding compound 2 by conjugate addition of a reagent of formula $R_2H$, or a salt thereof, where $R_2$ is as defined previously. Thus, when $R_2$ is a group —S—Ar, —S-Het, —S—$CH_2$—Ar or —S—$CH_2$-Het, the reagent is the corresponding thiol, or a salt thereof; when $R_2$ is O—Ar, the reagent is the corresponding aromatic carbinol; when $R_2$ is 2,5-dioxo-1-imidazolidinyl or a substituted derivative thereof, the reagent is the corresponding 2,4-imidazolidinedione. Said conversion from a compound 2 into a compound 4 can be accomplished, under identical or similar conditions, either when n in 2 is zero or it is 2; however, the preparation of compounds of formula (I) wherein $R_2$ is sulfanyl is better performed from compounds 2 where n is 2, because otherwise it is difficult to discriminate between the two sulfur atoms in the following oxidative step. Typically, the conjugate addition of said mercaptans and aromatic carbinols to a compound of formula 2 is accomplished using the reagents neat, or in a suitable organic solvent such as DCM, DMN, toluene, tetrahydrofuran (THF), acetonitrile (MeCN), methanol or ethanol, at temperatures ranging from ambient to reflux, in the absence or presence of a suitable base such as sodium bicarbonate, sodium carbonate, TEA, sodium methoxide or sodium ethoxide, preferably under a nitrogen blanket. When the reagent is 2,4-imidazolidinedione or a substituted derivative thereof, the conjugate addition to a compound 2 is preferably performed in toluene or DMF in the presence of a suitable base such as sodium bicarbonate, TEA, NMM and the like, at a temperature ranging from ambient to reflux, preferably between 50 and 110° C.; alternatively, a preformed salt of said reagent can be used, especially sodium, potassium and lithium salts, which can be obtained by treatment with suitable strong bases, especially sodium hydride, potassium hexamethyldisilazide, potassium tert-butoxide and butyllithium, in a suitable organic solvent.

When a compound 4 where n is zero is obtained by the methods above, it may be converted, if desired, into the corresponding compound where n is 2 by oxidation, under the same conditions described previously for the oxidation of a compound 2 where n is zero to a compound where n is 2.

Alternatively, a compound 4 can be obtained from a compound 1 through the intermediacy of a compound 3. This alternative route provides advantages when the reagent $R_2H$ is reluctant to the conjugate addition to a compound 2, e.g. when $R_2H$ is 2,5-dioxo-1-imidazolidine, and particularly when it is 4,4-dimethyl-2,5-dioxo-1-imidazolidine and the N-alkyl derivatives thereof. In the first step, said reagent $R_2H$ is condensed with the bromomethylacrylate 1 to provide 3. Typically, the reaction is performed in a solvent such as DMF or toluene, at temperatures ranging from 50° C. to reflux, and preferably in the presence of sodium bicarbonate. In the following step, conjugate addition of the suitable aryl-thiol to the intermediate 3 provides a compound 4 where n is zero. This reaction can be performed under the same conditions described above for reaction of 2 with a mercaptane $R_2H$ to provide 4.

Compounds 4 where R is a hydrogen atom and n is 2 are specifically represented by structure 5 and as such are a first object of this invention, i.e. the compounds of formula (I) wherein X is hydroxy (the 'carboxylates'). Compounds 4 where R is the residue of a carboxylic ester, as defined previously, and n is 2, are converted to said final compounds 5 by hydrolysis, according to the general methods known in the art such as using 6N HCl in acetic acid and refluxing for 10 to 20 hours or using iodotrimethylsilane in chloroform. When the R group is benzyl and $R_2$ is not a sulfanyl residue, a preferred method to obtain the free acid is hydrogenolysis, especially in the presence of a palladium catalyst such as Pd on charcoal, in an inert organic solvent such as ethanol or DMF or the like, typically at room temperature and under atmospheric pressure or moderate pressure. When the R group is tert-butyl, a preferred method for obtaining the free acid is reaction with HCl or trifluoroacetic acid, in inert organic solvents such as DCM, THF, MeCN and the like, optionally in admixture with water, methanol or ethanol, at temperatures ranging from −20 to +40° C.

Compounds 4 where R is the residue of a carboxylic ester and n is zero are converted to compounds 5 by a two-step procedure involving oxidation and hydrolysis, or hydrolysis and oxidation, as preferred. Conditions for oxidation and hydrolysis are the same as described above.

Compounds 4 where R is a hydrogen atom and n is 2, which have structure 5, are converted to compounds 6, which specifically represent the second object of this invention, i.e. structure (1) wherein X is —NHOH (the 'hydroxamates'), by activation of the acid and coupling with hydroxylamine or an O-protected derivative thereof. This reaction can be performed by several routes well known to those skilled in the art. For example, the acid can be activated as its chloride or a mixed anhydride. A preferred method for activation as the acid chloride is reaction with oxalyl chloride, typically in DCM containing DMF as a catalyst, at 0° C. to ambient temperature. A preferred method for activation as a mixed anhydride is reaction with a chlorocarbonate such as chloroethylformate in anhydrous TBF or a similar compatible solvent, in the presence of a tertiary amine such as TEA, NMM and the like. Alternatively, the acid can be activated by a carbodiimide condensing agent such as dicyclohexylcarbodiimide (DCC) or 1-(3-dimethylaminopropyl)-3-ethylcarbodiimide hydrochloride (WSCDI, water soluble carbodiimide), preferably in the presence of 1-hydroxybenzotriazole (HOBt) in an inert organic solvent such as DNEF at 0° C. to room temperature. Another method for the activation of the acids of formula 4 where R is hydrogen is reaction with benzotriazolyl-1-yloxy-tris(dimethylamino)phosphonium hexafluorophosphate (BOP reagent) in a suitable organic solvent such as MeCN, THF or DCM in the presence of a tertiary amine such as TEA or NMM. A further method is reaction with O-benzotriazolyl-N,N,N',N'-tetramethyluronium hexafluorophosphate (HBTU) or O-benzotriazolyl-N,N,N',N'-tetramethyluronium tetrafluoroborate (TMTU), under conditions similar to those described for the BOP reagent. When the activation is performed with oxalyl chloride, the acid chloride is usually isolated crude before reaction with the hydroxylamine reagent; when with chloroethylformate, EDC or WSCDI, the hydroxylamine reagent is preferably added after about 1 hour at room temperature; when with the BOP reagent, HBTU or TBTU, the hydroxylamine reagent is O-protected and it is preferably added from the beginning. Suitable O-protected hydroxylamines are O-(benxyl) benzylhydroxylamine, O-(tert-butyl)hydroxylamine, O-(tetrahydropyranyl)hydroxylamine, O-(trimethylsilyl) hydroxylamine and O-(tert-butyldimethylsilyl)-hydroxylamine, the first two being preferably used as their hydrochlorides and freed in situ by a tertiary amine such as TEA or NMM. Alternatively, when activation of the acid is performed with oxalyl chloride or WSCDI, the unprotected hydroxylamine (e.g., as the commercial 50% solution in water) or the hydrochloride thereof can be used, either in the organic solvents specified above or after dissolution in water or in a mixture of water and THF. Suitable conditions for the condensation step vary according to the activation method. Typically, when activation is by the acid chloride method, the reaction is fast and is complete within 1–5 hours at temperatures ranging from 0° C. to 25° C.; otherwise it can be slower, usually requiring stirring overnight at ambient temperature or even 1–5 days. When an O-protected hydroxylamine is used in the condensation, the reaction affords O-protected hydroxamate derivatives, and the desired free-hydroxamates 6 are obtained after removal of the protecting group. In particular, when O-(benzyl) hydroxylamine is used, deprotection is performed by hydrogenolysis, preferably with a palladium catalyst such as 5% Pd on charcoal, 5% Pd on $BaSO_4$, or palladium hydroxide on carbon (Pearlman's catalyst), typically in methanol or ethanol. When O-(tert-butyl)hydroxylamine is used, the free hydroxamate can be obtained after treatment with neat or aqueous trifluoroacetic acid, or with HCl in DCM. When O-(tetrahydropyranyl)hydroxylamine is used, the free hydroxamate is rapidly obtained by reaction with 4N aqueous HCl in suitable organic solvents or mixtures thereof, e.g. dioxane and methanol. When O-(trimethylsilyl) hydroxylamine is used, deprotection is usually achieved during work up, e.g. by partitioning of the condensation mixture between ethyl acetate and diluted hydrochloric acid. When O-(tert-butyldimethylsilyl)hydroxylamine is used, deprotection can be achieved by HF or fluoride salts, preferably with tetrabutylammonium fluoride, in a suitable organic solvent such as THF, at temperatures ranging from –10 to +25° C.

Compounds 4 where R is a hydrogen atom and n is zero are converted to compounds 6 by a sequence involving oxidation at the sulfur atom, activation of the carboxy group, condensation of the activated carboxy group with hydroxylamine or an O-protected derivative thereof and, when required, unmasking of the free hydroxamic group. The oxidation can be performed first, i.e. on said compounds of formula 4, as described previously for the oxidation of a compound of formula 2 where n is zero to the corresponding compound where n is 2. Alternatively, the oxidation can be performed at a later stage, i.e. on the O-protected or free hydroxamic acid, in which case a preferred oxidant is oxone, in a suitable organic solvent such as DMF, mixture of water and one or two water miscible organic solvents, such as methanol, ethanol, DMF and THF, at a temperature ranging from 5 to 25° C. Conditions for the other steps of the sequence, i.e. activation of the carboxy group, coupling with hydroxylamine or a protected derivative thereof and, if required, deprotection, are the same as described previously.

SCHEME I

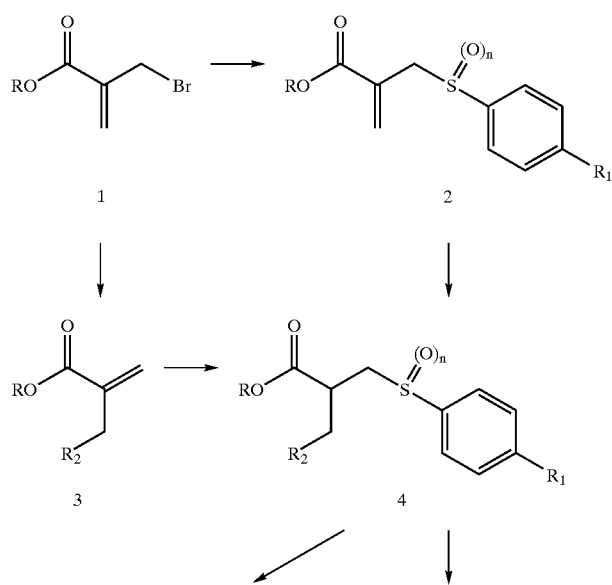

-continued

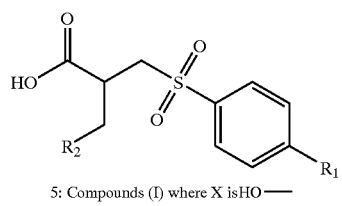

5: Compounds (I) where X is HO—

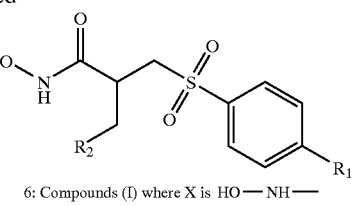

6: Compounds (I) where X is HO—NH—

In some cases, minor modifications of the general procedure indicated in Scheme I can be used to obtain compounds 4. For example, conversion of a compound 2 into a compound 4 wherein $R_2$ is a sulfanyl residue can be achieved in two steps, the first involving addition of HBr to a compound 2 to obtain the bromomethyl derivative, which is then reacted with the thiol which $R_2H$ can represent. This two-step procedure can be convenient for less reactive thiols, in particular when $R_2$ is $SCH_2$—Ar or —S—$CH_2$-Het. A preferred solvent for the addition of HBr to a compound 2 is acetic acid, usually at ambient temperature. The thiol is preferably reacted with said bromomethyl intermediate in the presence on an organic or inorganic base such as TEA, NMM, sodium bicarbonate, potassium carbonate and the like. Less reactive thiols can be advantageously reacted after conversion to salts thereof, e.g. by treatment with potassium hexamethyldisilazide at low temperature in a suitable organic solvent such as THF, and reacted in situ with the compound 2. The bromomethyl intermediate, or the corresponding carbinol, can also be used to obtain compounds 4 wherein $R_2$ is 2,5-dioxo-1-imidazolidinyl. In particular, the bromomethyl derivative can be reacted with 2,4-imidazolidinedione, or a derivative thereof, under conditions similar to that described above for reaction with a thiol, and the carbinol can be condensed with the same reagent under Mitsunobu conditions, i.e. in the presence of triphenylphosphine and diethyl azodicarboxylate in DMF a temperatures ranging from 0 to 25° C.

The compounds of formula (I) wherein $R_2$ is 2,4-dioxo-1-imidazolidinyl can be obtained by the variant described in Scheme II below. As therein outlined, an aminoacid $H_2N$—$CHR_3$—COOH where $R_3$ is a hydrogen atom, $C_{1-4}$ straight or branched alkyl or benzyl, or a salt or an ester thereof, especially the methyl or ethyl esters, is condensed with is compound 1, as defined in Scheme I, to obtain a compound 7 where R, $R_3$ are as above defined, and R' is either a hydrogen atom or methyl or ethyl. This reaction is carried out in a suitable organic solvent, with or without a base, at temperatures ranging from 0 to 50° C., preferably around ambient temperature. A preferred solvent is DMF; preferred bases, which can be present in amounts variable to a catalytic one to 3 molar equivalents, are tertiary amines, such as TEA, NMM, Hunig's base and the like. The obtained compound 7 is then reacted with sodium or potassium cyanate, or with an isocyanate of formula $R_4$—NCO where $R_4$ is $C_{1-4}$ alkyl, phenyl or benzyl, to obtain an intermediate urea, which is cyclized to a compound 8 where R, $R_3$ and $R_4$ are as defined above, in a suitable organic solvent such as THF, dioxane, MeCN, DMF and the like, at temperatures ranging from about 20° C. to reflux. Said compound 8 is then reacted with an aryl thiol of formula $R_1$—$C_6H_4$—SH to obtain a compound 9 where $R_1$ is as above defined and n is zero. Typically, the conjugate addition of said aryl thiol to a compound 8 is accomplished in a suitable organic solvent such as DCM, DMF, toluene, tetrahydrofuran (THF), acetonitrile (MeCN), methanol or ethanol, at temperatures ranging from ambient to reflux, in the absence or presence of a suitable base such as sodium bicarbonate, sodium carbonate, TEA, sodium methoxide or sodium ethoxide, preferably under a nitrogen blanket. Conversion of a compound 9 where n is zero into a compound 9 where n is 2 is accomplished under the conditions previously described in Scheme I, preferably with Oxone® in an organic solvent such as DUF or in a mixture of water and water-miscible organic solvent such as methanol, DMF or the combination of two, at ambient temperature or under moderate heating. Alternatively, the same synthetic sequence is carried out on a compound 2, as defined in Scheme I, to obtain the same compound 9 via 10. Compounds 9 where n is two and R is a hydrogen atom are the desidered compounds of formula (I) where X is HO— and $R_2$ is 2,4-dioxoimidazolidin-1-yl. The corresponding compounds of formula (I) where X is HONH— are obtained, if desired, as described previously (Scheme I) for the conversion of a compound 5 into a compound 6.

SCHEME II

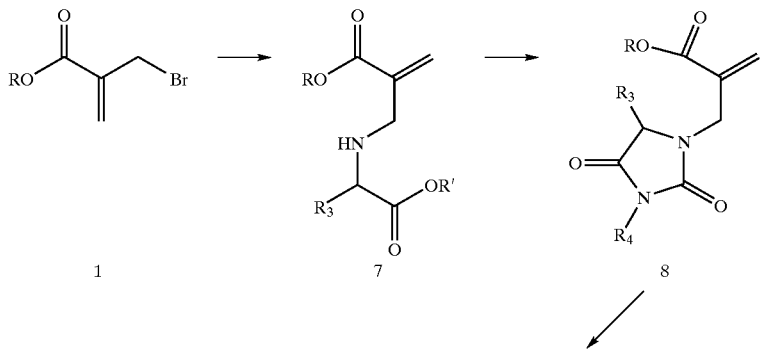

1          7          8

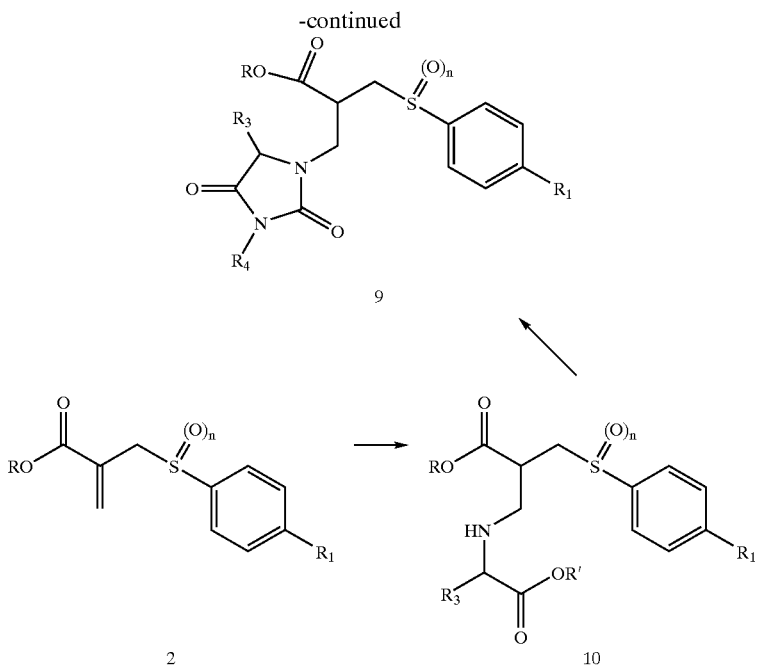

When required or convenient, chemical modifications of the group $R_1$ or $R_2$ in intermediates 2, 3, 4 and 9 can be performed in the above processes to obtain the final compounds of formula (I). For example, a compound 3 or 4 wherein $R_2$ is 2,5-dioxo-1-imidazolidinyl having the 3-nitrogen atom unsubstituted can be alkylated at said atom to obtain the corresponding N-alkyl derivatives, e.g. with methyl iodide in DMF in the presence of potassium carbonate. When $R_1$ and $R_2$ in the final compounds of formula (I) are, or contain, a reactive functional group, e.g. amino and hydroxy, these groups can be protected at the appropriate stage and unmasked when convenient, according to conventional methods well known in the art.

The chemistry in Scheme I and II proceeds through achiral or racemic intermediates, unless a substituent in $R_1$ or $R_2$ is chiral and enantiopure, or the aminoacid used in Scheme I for the preparation of compound 7 or 10 is chiral and enantiopure. When desired, pure enantiomers of the final products, in particular compounds of formula (I') above, may be obtained from racemic compounds (I), or racemic intermediates thereof, by methods well known to one skilled in the art. For example, racemic carboxylates, including compounds (I) where X is HO— and intermediates 4, 9 where R is a hydrogen atom and n is zero, or intermediates 10 where R is a hydrogen atom, can be resolved by chiral salt formation, for example with enantiopure 1-phenylethylamine, brucine, ephedrine, strychnine, morphine. Alternatively, final racemic compounds or racemic intermediates can be resolved by chiral chromatography. By another method, carboxylic esters, preferably methyl, ethyl and butyl esters, can be selectively hydrolysed to chiral acids by lipases and esterases. By a still different procedure, racemic carboxylic acids can be converted to diastereomeric esters with chiral alcohols such as borneol, menthol and the like, which are then separated by crystallization or conventional chromatography. Alternatively, when in the acrylates of formula 2, 3, 8 in Schemes I and II R is the residue of a chiral alcohol such as borneol, menthol and the like, diastereomeric compounds 4, 9 10 are obtained, and variable degrees of diastereoselectivity can be achieved.

The present invention further provides a compound of formula (I) as defined above for use in a method of treatment or prophylaxis of a disease mediated in a mammal by a matrix metalloproteinase, especially the gelatinases (MMP-2 and MMP-2), the membrane-type M involved in gelatinase activation (MMP-14), the stromelysins (MMP-3 and MMP-10), collagenase-3 (MMP-13) and neutrophyl collagenase (MMP-8). Diseases for which the compounds of the present invention are particularly intended are: tumor growth and metastasis; rheumatoid arthritis and osteoarthritis; ophthalmic diseases, in particular age-related macular degeneration and diabetic retinopathy; cardiovascular diseases, in particular restenosis; periodontal diseases; multiple sclerosis; Alzheimer disease.

The compounds of the present invention are typically administered in the form of pharmaceutical compositions, which can be prepared by combining the compounds of formula (I) or (I') or salts or hydrates or solvates thereof with a solid or liquid pharmaceutically acceptable career, and, optionally, with pharmaceutically acceptable adjuvants and excipients, employing standard and conventional techniques. In particular, said compounds can be administered:

a) orally, for example, as tablets, coated tablets, capsules, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil. Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpynolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl or n-propyl p-hydroxybenzoate, one or more coloring agents, one or more flavoring agents, or one or more sweetening agents, such as sucrose or saccharin. Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present. The pharmaceutical compositions of the invention may also be in the form of oil-in-water emulsions The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavoring agents. Syrups and elixirs may be formulated with sweetening agents, for example glycerol, sorbitol or sucrose. Such formulations may also contain a demulcent, a preservative and flavoring and coloring agents;

b) parenterally, either subcutaneously, or intravenously, or intramuscularly, or intrastemally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

c) topically, in the form of creams, ointments, jellies, plasters, collyriums, solutions or suspensions;

d) rectally, in the form of suppositories prepared by mixing the drug with a suitable non-irritating excipient which is solid at ordinary temperature but liquid at the rectal temperature and will therefore melt in the rectum to release the drug. Such materials are cocoa butter and polyethylene glycols.

The compounds of this invention are advantageously administered orally in solid and liquid dosage forms. Daily dosages can vary within wide limits and will be adjusted to the individual requirements in each particular case. As a rule of thumb, a compound of formula (I) or (I') is advantageously administered at a dosage and frequency to achieve and maintain, for the whole period of therapy, a blood level in free drug (i.e., not bound to plasma proteins) ranging from about 1 to about 100 times its Ki against the most relevant MMP for the particular disease state, e.g. MMP-2 for cancer. Thus, the daily dose may be divided into multiple doses for administration, e.g. two to four times per day, which is generally expedient for compounds of formula (I) or (I') wherein X is HO—NH—; or, in the case of particularly favorable pharmacokinetics, which can be found in compounds of formula (I) or (I') wherein X is HO—, the drug can be given daily, or even at alternate days. Generally, an amount of the active compound effective in adult patients will be in the range of 1 to about 500 mg, but it is to be understood that such range may be exceeded depending on the particular compound being used, the severity of the disease being treated, and the requirement of the patient.

The compounds of the present invention and their preparation will be better understood in connection with the following examples, which are intended as an illustration of and not a limitation upon the scope of the invention.

EXAMPLE 1

Preparation of 3-[(4'-chloro[1,1'-biphenyl]-4-yl)sulfonyl]-2-[(phenylsulfanyl)methyl]propanoic acid

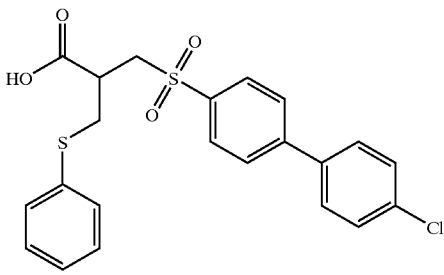

Step 1. 4'-Chloro[1,1'-biphenyl]-4-sulfonic acid.

To a stirred solution of 4-chlorobiphenyl (21 g) in 150 mL of chloroform, cooled at −5° C., was added dropwise chlorosulfonic acid (10.2 mL, 1.36 eq.). The cooling bath was removed and the mixture was stirred for 1 hour. Evaporation in vacuo left the title compound as a syrup.

Step 2. 4'-Chloro[1,1'-biphenyl]-4-sulfonyl chloride.

The crude product from step 1 was dissolved in thionyl chloride (100 mL) and refluxed for 1 hour. The solvent was removed in vacuo and the resulting solid was stripped twice with toluene (150 mL).

Step 3. 4'-Chloro[1,1'-biphenyl]-4-thiol.

4'-Chloro[1,1'-biphenyl]-4-sulfonyl chloride (30 g) was added portion wise to a stirred solution of tin(II) chloride dihydrate (80 g) in conc. HCl (50 mL) and water (150 mL) at 90–95° C. The resulting yellow slurry was stirred for 1 hour at the same temperature. After cooling, the precipitate was collected by filtration, thoroughly washed with water and dried to afford 21 g of bis[4-(4'-chloro[1,1'-biphenyl])]disulfide, m.p. 164–166° C. This material was dissolved in THF 8200 mL) and conc. HCl (25 mL), and Zn powder (20 g) was added under stirring. After stirring for 30 minutes at ambient temperature, the Zn was removed and rinsed with THF. The clear solution was concentrated in vacuo and partitioned between chloroform (450 mL) and brine. The organic phase was dried over anhydrous sodium sulfate and evaporated to leave 19 g of the title compound, mp 154–157° C.

Step 4. 2-[[(4'-Chloro[1,1'-biphenyl]-4-yl)sulfanyl]methyl]acrylic acid.

The thiol from step 3 (22 g) and 2-(bromomethyl)acrylic acid (1–8 g) were dissolved in 100 mL of DMF and stirred at 30° C. for 2 days under a low stream of nitrogen. The reaction mixture was diluted with ethyl acetate (400 mL) and washed several times with brine until neutral. The organic phase was dried over anhydrous sodium sulfate and evaporated in vacuo to obtain a crystalline mass. After addition of diethyl ether (150 mL) and swirling, the solid was collected by filtration, washed twice with ether, and dried to afford 21 g of the title compound, mp 191–195° C.

Step 5. 2-[[(4'-Chloro[1,1'-biphenyl]-4-yl)sulfonyl]methyl]acrylic acid.

The material from step 4 above (20 g) was dissolved in 100 mL of DMF and added dropwise to a stirred solution of Oxone® (105 g) in 300 mL of water at 45–50° C. After stirring for 5 hours, water (1 L) was added. The solid was collected by filtration, washed several times with water, then twice with ethanol (100 mL) and dried to provide 21.5 g of the title compound, mp 178–181° C.

Step 6. 3-[(4'-Chloro[1,1'-biphenyl]-4-yl)sulfonyl]-2-[(phenylsulfanyl)methyl]propanoic acid.

Under a low stream of nitrogen, thiophenol (20 mL) was added to a stirred solution of the material from step 5 above (20 mg) in 35 mL of DMF. After stirring at 35° C. for 2 days, the reaction mixture was diluted with ethyl acetate and treated dropwise with a solution of iodine (21 g) in 75 mL of THF. The resulting brown solution was washed until complete decolorization with a solution of sodium metabisulfite (10 g) in 300 mL of water. After washing with brine and drying over anhydrous sodium sulfate, the solvent was removed and the residue was filtered through a short pad of silica gel (450 g), eluting with chloroform, to obtain 23 g of the title compound, mp 158–162° C.

$^1$H NMR (400 MHz, CDCl$_3$): δ 3.06 (m, 2H), 3.33 (m, 1H), 3.60 (dd, J=3.4 and 14.2 Hz, 1H), 3.68 (dd, J=7.3 and 14.2 Hz, 1H), 7.22 (m, 5H), 7.50 (m, 4H), 7.68 (d, J=8.4 Hz, 2H), 7.88 (d, J=8.4 Hz, 2H) [COOH: not seen]. MS (EI): m/z 446, 252, 194, 152, 149, 110. Anal. Found C, 59.32; H, 4.44; S, 14.32.

EXAMPLE 2

Preparation of Sodium 3-[(4'-chloro[1,1'-biphenyl]-4-yl)sulfonyl]-2-[(phenylsulfanyl)methyl]-propanoate Sodium hydroxide (1 M, 48 mL) was added to a solution in methanol (75 mL) of 3-[(4'-chloro[1,1'-biphenyl]-4-yl)sulfonyl]-2(RS)-[(phenylsulfanyl)-methyl]propanoic acid (20 g, obtained as described in Example 1). Charcoal was added and the mixture was filtered. Concentration of the filtrate to 1/3 of the original volume furnished a shiny precipitate, which was collected by filtration and sequentially washed with cold water, ethanol and diethyl ether. Drying to a constant weight provided 19 g of the title compound as white crystals.

EXAMPLE 3

Preparation of (2S)-3-[(4'-chloro[1,1'-biphenyl]-4-yl)sulfonyl]-2-[(phenylsulfanyl)methyl]propanoic acid and of (2R)-3-[(4'-chloro[1,1'-biphenyl]-4-yl)sulfonyl]-2-[(phenylsulfanyl)-methyl]propanoic acid Racemic 3-[(4'-chloro[1,1'-biphenyl]-4-yl)sulfonyl]-2-[(phenylsulfanyl)methyl]propanoic acid, prepared as described in Example 1, was eluted over Chiralpak AS (Chiral Technologies) with ethanol +0.05% trifluoroacetic acid (V/V) at 0.4 mL/min, monitoring the absorbance at 270 nm. The eluates were collected and concentrated in vacuo to yield the title enantiomers.

ISOMER 1, (2S) Configuration:

R$_f$=12.0 min (0.46×25 cm Chiralpak AS, ethanol+0.05% TFA); [α]$^{25}_D$=+47.8° (c=0.83%, EtOH). Absolute configuration established by X-Ray crystallography.

ISOMER 2, (2R) Configuration:

R$_f$=15.0 min (0.46×25 cm Chiralpak AS, ethanol+0.05% TFA); [α]$^{25}_D$=−43° (c=0.83%, EtOH).

EXAMPLE 4

Preparation of 3-[(4'-chloro[1,1'-biphenyl]-4-yl)sulfonyl]-N-hydroxy-2-[(phenylsulfanyl)methyl]propanamide

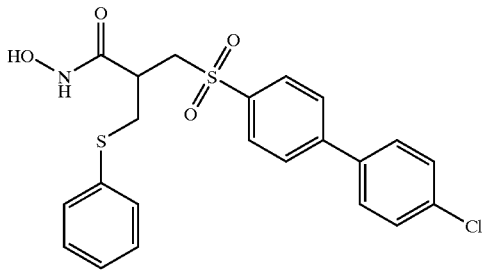

TBTU (0,72 g) was added portionwise to a stirred solution of N-methylmorpholine (0.5 mL) and O-tert-butylhydroxylamine hydrochloride (0.43 g) and 3-[(4'-chloro[1,1'-biphenyl]-4-yl)sulfonyl]-2-[(phenylsulfanyl)methyl]-propanoic acid (0.5 g) in 20 mL of DMF and 20 mL of acetonitrile cooled at −5° C. After stirring at ambient temperature overnight, the resulting solution was diluted with ethyl acetate and sequentially washed with 0.1 M citric acid and 0.1 M NaHCO$_3$. After drying over anhydrous sodium sulfate and removal of the solvent, the crude reaction mixture was treated with trifluoroacetic acid (10 mL) and kept aside for 6 hours. The solvent was removed and the residue was partitioned between ethyl acetate and 0.1 M NaHCO$_3$. After drying, the solvent was evaporated off and the residue was chromatographed on silica gel eluting with chloroform/cyclohexane 2/3 to afford, after crystallization from ethyl acetate, 0.35 g of the title compound, mp . . .

$^1$H NMR (400 MHz, DMSO-d$_6$): δ 2.70(m, 1H), 3.09 (d, J=7.8 Hz, 2H), 3.61 (m, 2H), 7.20 (m, 5H), 7.58 (d, J=8.3 Hz, 2H), 7.78 (d, J=8.3 Hz, 2H), 7.90 (m, 4H), 8.95 (s, 1H), 10.81 (s, 1H). MS (EI): m/z 461, 400.

EXAMPLE 5

Preparation of 3-[(4'-chloro[1,1'-biphenyl]-4-yl)sulfonyl]-2-[(3,4,4-trimethyl-2,5-dioxo-1-imidazolidinyl)methyl]propanoic acid

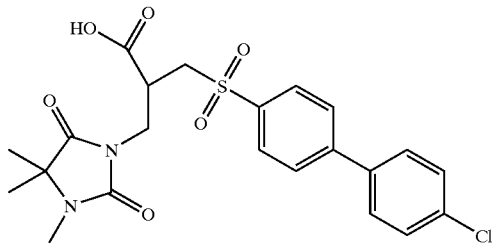

Step 1. 3-[(4'-Chloro[1,1'-biphenyl]-4-yl)sulfanyl]-2-[(3,4,4-trimethyl-2,5-dioxo-1-imidazolidinyl)methyl]propanoic acid.

To a stirred solution of α-bromomethylacrylic acid (1.65 g) and NaHCO$_3$ (1.7 g) in 25 mL of DMF was added 3,4,4-trimethyl-2,5-dioxo-1-imidazolidine (2.13 g) and the resulting suspension was heated at 75° C. for 3 h. After disappearance of α-bromomethylacrylic acid, checked by tlc and HPLC, the solution was cooled at 0–5° C. and 4'-chloro[1,1'-biphenyl]-4-thiol (3.3 g) was added. After stirring overnight at room temperature, the solution was diluted with ethyl acetate and washed thoroughly with 0.1 M citric acid. After drying and removal of the solvent, the residue was chromatographed on silica gel eluting with chloroform/cyclohexane 1/1 to provide, after crystallization from ethyl ether, 2.4 g of the title compound, mp 148–150° C.

Step 2. 3-[(4'-Chloro[1,1'-biphenyl]-4-yl)sulfonyl]-2-[(3,4,4-trimethyl-2,5-dioxo-1-imidazolidinyl)methyl]propanoic acid.

A solution of 3-[(4'-chloro[1,1'-biphenyl]-4-yl)sulfanyl]-2-[(3,4,4-trimethyl-2,5-dioxo-1-imidazolidinyl)methyl]propanoic acid (4.6 g) in 30 ml of DMF was added dropwise to a stirred solution of Oxone® (13.5 g) in 75 mL of DMF and 20 mL of water at 45° C. After stirring for 2 h, the solvent was removed and the residue was partitioned between ethyl acetate and brine. The residue was columned on a small pad of silica gel eluting with chloroform to furnish 3.9 g of the title compound as a white foam.

$^1$H NMR (400 MHz, DMSO-d$_6$): δ 1.22(s, 3H) 1.24 (s, 3H), 2.74 (s, 3H), 3.02 (m, 1H), 3.5–3.7 (m, 4H), 7.57 (d, J=8.3 Hz, 2H), 7.79 (d, J=8.3 Hz, 2H), 7.94 (m, 4H), 12.85 (broad s, 1H). MS (EI): m/z 478, 433, 252, 211, 152, 56. Anal. Found C, 54.89; H, 5.15; N, 5.64; S, 6.53.

EXAMPLE 6

Preparation of (2R)-3-[(4'-chloro[1,1'-biphenyl]-4-yl)sulfonyl]-2-[(3,4,4-trimethyl-2,5-dioxo-1-imidazolidinyl)methyl]propanoic acid and of (2S)-3-[(4'-chloro[1,1'-biphenyl]-4-yl)sulfonyl]-2-[(3,4,4-trimethyl-2,5-dioxo-1-imidazolidinyl)methylpropanoic acid Racemic 3-[(4'-chloro[1,1'-biphenyl]-4-yl)sulfonyl]-2-[(3,4,4-trimethyl-2,5-dioxo-1-imidazolidinyl)methyl]propanoic acid, prepared as described in Example 5, was separated by chiral chromatography under the conditions described in Example 3.

ISOMER 1, (2R) Configuration:
R$_f$=9 min (0.46×25 cm Chiralpak AS, ethanol+0.05% TFA); [□]$^{25}$$_D$=−8.7° (c=0.83%, EtOH). The absolute configuration established by protein X-Ray in complex with truncated stromelysin (MMP-3).

ISOMER 2, (2S) Configuration:
R$_f$=12 min (0.46×25 cm Chiralpak AS, ethanol+0.05% TFA); [□]$^{25}$$_D$=+8.2° (c=0.83%, EtOH).

EXAMPLE 7

Preparation of 3-([1,1'-biphenyl-4-ylsulfonyl)-2-[(3,4,4-trimethyl-2,5-dioxo-1-imidazolidinyl)methyl]propanoic acid

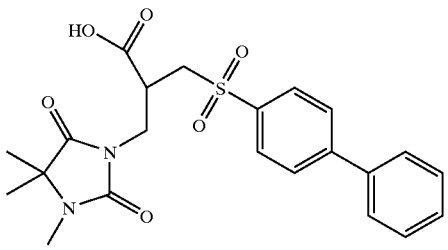

Following the general procedure outlined in Example 5 and making non-critical variations but replacing 4'-chloro[1,1'-biphenyl]-4-thiol with [1,1'-biphenyl)]thiol in step 2, the title compound was obtained as a whitish crystalline powder, mp>200° C. (dec.).

¹H NMR (400 MHz, DMSO-d₆): δ 1.16 (s, 3H), 1.17 (s, 3H), 2.68 (s, 3H), 2.96 (m, 1H), 3.43 (dd, J=3.6 and 14.6 Hz, 1H), 3.54 (m, 2H), 3.63 (dd, J=8.7 and 14.6 Hz, 1H), 7.40 (m, 3H), 7.70 (m, 2H), 7.87 (m, 4H), 12.90 (broad s, 1H). MS (EI): m/z 445, 427, 227, 209. Anal. Found C, 57.39; H, 5.66; N, 6.98; S, 5.95.

EXAMPLE 8

Preparation of 3-[(4'-chloro[1,1'-biphenyl]-4-yl)sulfonyl]-N-hydroxy-2-[(3,4,4-trimethyl-2,5-dioxo-1-imidazolidinyl)methyl]propanamide

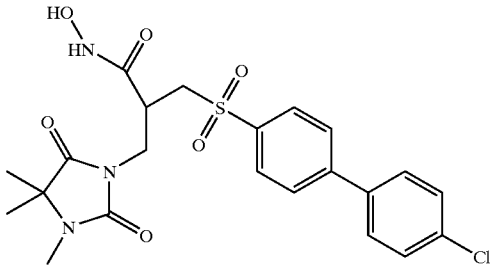

Following the general procedure outlined in Example 4 and making non-critical variations but replacing 3-[(4'-chloro[1,1'-biphenyl]-4-yl)sulfonyl]-2-[(phenylsulfanyl)methyl]propanoic acid with 3-[(4'-chloro[1,1'-biphenyl]-4-yl)sulfonyl]-2-[(3,4,4-trimethyl-2,5-dioxo-1-imidazolidinyl)methyl]propanoic acid, the title compound was obtained as a white crystalline powder.

¹H NMR (400 MHz, DMSO-d₆): δ 1.19 (s, 3H), 1.22 (s, 3H), 2.72 (s, 3H), 2.90 (m, 1H), 3.38 (dd, J=2.9 and 14.6 Hz, 1H), 3.46 (m, 2H), 3.60 (dd, J=8.3 and 14.6 Hz, 1H), 7.57 (d, J=8.3 Hz, 2H), 7.78 (d, J=8.3 Hz, 2H), 7.93 (m, 4H), 8.82 (s, 1H), 10.80 (s, 1H). ESI(+)-MS: m/z 494, 4.61, 235, 209. Anal. Found C, 43.58; H, 4.12; N, 6.61; S, 5.10.

EXAMPLE 9

Preparation of 3-[(4'-chloro[1,1'-biphenyl]-4-yl)sulfonyl]-2-[(4,4-dimethyl-2,5-dioxo-1-imidazolidinyl)methyl]propanoic acid

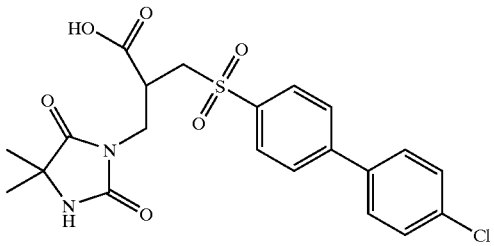

Following the general procedure outlined in Example 5 and making non-critical variations but starting with 5,5-dimethyl-2,4-imidazolidinedione in step 1, the title compound was obtained as a white crystalline powder, mp 242–245° C.

¹H NMR (400 MHz, DMSO-d₆): δ 1.21(s, 3H), 1.22 (s, 3H), 3.04 (m, 1H), 3.52 (m, 1H), 3.57 (m, 1H), 3.68 (m, 1H), 7.58 (d, J=8.5 Hz, 2H), 7.79 (d, J=8.5 Hz, 2H), 7.94 (m, 4H), 8.29 (s, 1H), 12.82 (broad s, 1H). ESI(+)-MS: m/z 465, 235, 213, 213, 195. Anal. Found C, 52.30; H, 4.82; N, 5.76; S, 6.44.

EXAMPLE 10

Preparation of 3-[(4'-chloro[1,1'-biphenyl]-4-yl)sulfonyl]-N-hydroxy-2-[(4,4-dimethyl-2,5-dioxo-1-imidazolidinyl)methyl]propanamide

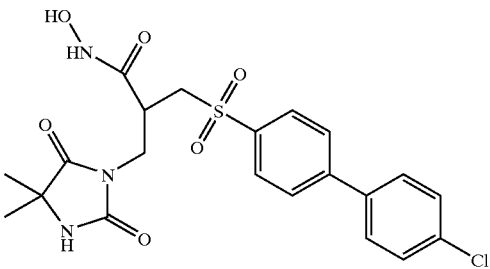

Following the general procedure outlined in Example 7 and making non-critical variations but starting in step 1 with 3-[(4'-chloro[1,1'-biphenyl]-4-yl)sulfonyl]-2-[(4,4-dimethyl-2,5-dioxo-1-imidazolidinyl)methyl]propanoic acid (prepared as described in Example 8), the title compound was obtained as a white crystalline powder.

¹H NMR (400 MHz, DMSO-d₆): δ 1.17(s, 3H), 1.21 (s, 3H), 3.34 (dd, J=3.0 and 15.0 Hz, 1H), 3.44 (m, 2H), 3.62 (dd, J=9.0 and 15.0 Hz, 1H), 7.58 (d, J=8.9 Hz, 2H), 7.78 (d, J=8.9 Hz, 2H), 7.93 (m, 4H), 8.24 (s, 1H), 8.83 (s, 1H), 10.81 (s, 1H). ESI(+)-MS: m/z 480, 447, 195. Anal. Found C, 54.06; H, 4.87; N, 8.67; S, 6.96.

EXAMPLE 11

Preparation of 3-[(4'-chloro[1,1'-biphenyl]-4-yl)sulfonyl]-2-[(2,5-dioxo-1-imidazolidinyl)methyl]propanoic acid

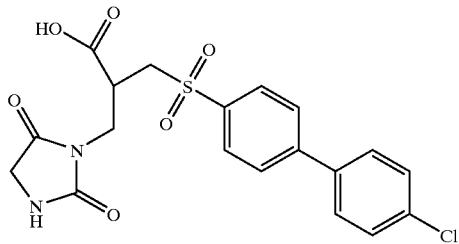

Following the general procedure outlined in Example 5 and making non-critical variations but starting with 2,4-imidazolidinedione in step 1, the title compound was obtained as a white crystalline powder, mp 188–190° C.

¹H NMR (400 MHz, DMSO-d₆): δ 3.02 (m, 1H), 3.5–3.7 (m, 4H), 3.82 (d, J=17.7 Hz, 1H), 3.87 (d, J=17.7 Hz, 1H), 7.59 (d, J=8.5 Hz, 2H), 7.80 (d, J=8.5 Hz, 2H), 7.94 (m, 4H), 8.07 (s, 1H), 12.80 (broad s, 1H). ESI(+)-MS: m/z 437, 419, 235, 167. Anal. Found C, 47.71; H, 3.81; N, 5.79; S, 7.18.

EXAMPLE 12

Preparation of 3-[(4'-chloro[1,1'-biphenyl]-4-yl)sulfonyl]-N-hydroxy-2-[(2,5-dioxo-1-imidazolidinyl)methyl]propanamide

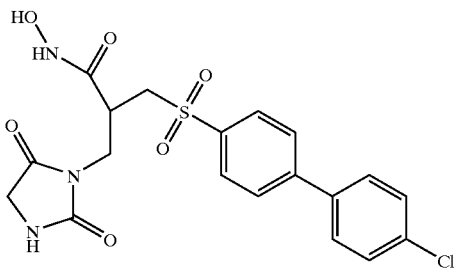

Following the general procedure outlined in Example 8 and making non-critical is variations but starting, in step 1 with 3-[(4'-chloro[1,1'-biphenyl]-4-yl)sulfonyl]-2-[(2,5-dioxo-1-imidazolidinyl)methyl]propanoic acid (prepared as described in Example 11), the title compound was obtained as a yellowish crystalline powder, mp 150–156° C.

$^1$H NMR (400 MHz, DMSO-$d_6$): δ 2.83 (m, 1H), 3.37 and 3.60 (each m, 1H), 3.42 (m, 2H), 3.76 (d, J=17.6 Hz, 1H), 3.81 (d, J=17.6 Hz, 1H), 7.57 (d, J=8.3 Hz, 2H), 7.78 (d, J=8.3 Hz, 2H), 7.91 (m, 4H), 8.01 (s, 1H), 8.70 (broad s, 1H), 10.80 (broad s, 1H). ESI(+)-MS: m/z 452, 419, 235. Anal. Found C, 44.35; H, 3.87; N, 7.59; S, 6.81.

EXAMPLE 13

Preparation of 3-[(4'-chloro[1,1'-biphenyl])yl)sulfonyl]-2-[(3-butyl-2,5-dioxo-1-imidazolidinyl)methyl]propanoic acid

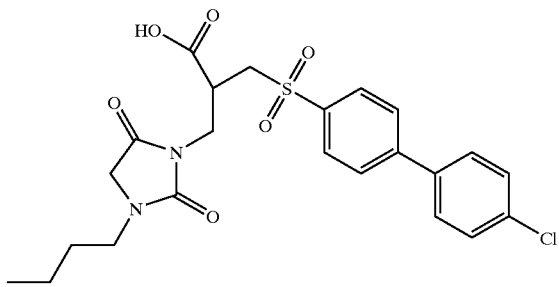

Step 1. Methyl 2-[(3-butyl-2,5-dioxo-1-imidazolidinyl)methyl]acrylate.

Methyl 2-(bromomethyl)acrylate (0.7 mL) and 1-butyl-2,4-imidazolidinedione (1 g) were dissolved in DMF (3 mL). Sodium hydrogen carbonate (693 mg) was added, and the mixture heated at 80° C. for 2 hours, cooled to ambient temperature and partitioned between ethyl acetate and water. The organic layer was washed with water and brine, dried over anhydrous sodium sulfate and evaporated in vacuo to leave the title compound (1.0 g) as a colourless oil.

Step 2. Methyl 3-[(4'-chloro[1,1'-biphenyl]-4-yl)sulfanyl]-2-[(3-butyl-2,5-dioxo-1-imidazolidinyl)methyl]propanoate.

The product from step 1 above (500 mg) and 4'-chloro[1,1'-biphenyl]-4-thiol (520 mg) were dissolved in DMF (5 mL). Sodium hydrogen carbonate (252 mg) was added, and the mixture heated at 60° C. for 1 hour, cooled to ambient temperature and partitioned between ethyl acetate and water. The organic layer was washed with water and brine, dried over anhydrous sodium sulfate and evaporated in vacuo to leave the crude title compound, which was used as such in the following step.

Step 3. Methyl 3-[(4'-chloro[1,1'-biphenyl]-4-yl)sulfonyl]-2-[(3-butyl-2,5-dioxo-1-imidazolidinyl)methyl]propanoate.

The crude compound from step 2 above was taken up in DMF (7 mL). Oxone® (2 g) was added, and the mixture stirred for 4 hours at ambient temperature. Work-up as in step 1 left a residue, which was purified by flash chromatography over silica (ethyl acetate-hexane), to obtain the title compound (650 mg) as a colorless foam.

Step 4. 3-[(4'-Chloro[1,1'-biphenyl]-4-yl)sulfonyl]-2-[(3-butyl-2,5-dioxo-1-imidazolidinyl)-methyl]propanoic acid.

2N Hydrochloric acid (5 mL) was added to a solution of the compound from step 3 above (650 mg) in acetic acid (2 mL), and the mixture was stirred at 80–90° C. After 2 hours, 37% HCl (1 mL) was added and stirring at 80° C. was continued for additional 5 hours. The reaction mixture was evaporated in vacuo, and the residue partitioned between ethyl actetate and water. The organic layer was dried over anhydrous sodium sulfate and evaporated. The solvent was removed in vacuo and the resulting solid was stripped twice with toluene, to yield the title compound (420 mg) as a whitish powder.

$^1$H NMR (400 MHz, DMSO-$d_6$): δ 0.84 (t, J=7.3 Hz, 3H), 1.07 (m, 2H), 1.41 (m, 2H), 2.99 (m, 1H), 3.20 (t, J=7.1 Hz, 2H), 3.4–3.7 (m, 4H), 3.88 (d, J=7.6 Hz, 1H), 3.92 (d, J=7.6 Hz, 1H), 7.58 (d, J=8.8 Hz, 2H), 7.80 (d, J=8.8 Hz, 2H), 7.93 (m, 4H), 12.95 (broad s, 1H). ESI(+)-MS: m/z 515, 493, 475, 223. Anal. Found C, 57.39; H, 5.66; N, 6.98; S, 5.95.

EXAMPLE 14

Preparation of 3-[[4-(Benzoylamino)phenyl]sulfonyl]-2-[(2-thienylsulfanyl)methyl]propanoic acid

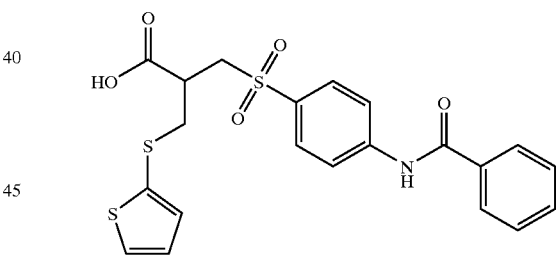

Step 1. Bis(4-benzoylamino)phenyl)disulfide.

Benzoyl chloride (8 mL) was added to a solution of bis(4-aminophenyl)disulfide (4 g) and TEA (10 mL) in 100 mL of dichloromethane, and the mixture was stirred for 2 hours at ambient temperature. The precipitate was collected by filtration and sequentially washed with water, diluted aqueous HCl and n-exane to obtain the title compound as a white solid.

Step 2. N-(4-Sulfanylphenyl)benzamide.

Zn powder (0.5 g) and 2 N HCl (30 mL) was added in three portions under vigorous stirring to a suspension of the disulfide from step 1 in THF (100 mL). After 4 hour at ambient temperature, the mixture was filtered and the filtrate was concentrated in vacuo. The residue was taken up in ethyl acetate and sequentially washed with water and aqueous sodium hydrogen carbonate. Drying over anhydrous sodium sulfate and evaporation afforded 3.66 g of the title compound as a yellow solid.

Step 3. 2-[[[4-(Benzoylamino)phenyl]sulfanyl]methyl] acrylic acid.

A mixture of N-(4-sulfanylphenyl)benzamide (1.5 g), 2-(bromomethyl)acrylic acid (1 g) and TEA (1.75 mL) was stirred for 4 hours at ambient temperature. Washing with diluted aqueous HCl, drying over anhydrous sodium sulfate and evaporation in vacuo left a residue, which was passed through a short pad of silica gel (dichloromethane-methanol as the eluants) to obtain 1.68 g of the title compound as a colorless oil.

Step 4. 2-[[[4-(Benzoylamino)phenyl]sulfonyl]methyl] acrylic acid.

A mixture of Oxone® (10 g) and 2-[[[4-(benzoylamino) phenyl]sulfanyl]methyl]acrylic acid (1.68 g) in DMF (20 mL) was heated at 50° C. for 4 hours under vigouros stirring, then partitioned between ethyl acetate and 4% aqueous HCl. The organic phase was washed twice with water, dried over anhydrous sodium sulfate and evaporated to obtain the crude title compound as a yellowish oil.

Step 5. 3-[[4-(Benzoylamino)phenyl]sulfonyl]-2-[(2-thienylsulfanyl)methyl]propanoic acid.

2-Thiophenethiol (250 mg) was added to a solution of the crude acrylic acid from step 4 above (300 mg) in 5 mL of DMF. After 1 hour at ambient temperature, the mixture was partitioned between ethyl acetate and 4% aqueous HCl. The organic phase was washed twice with water, dried over anhydrous sodium sulfate and evaporated: The residue was chromatographed over silica gel with chloroform/methanol, and the eluate concentrated in vacuo to obtain 335 mg of the tide compound as a yellowish powder.

$^1$H NMR (400 MHz, DMSO-d$_6$): δ 2.70 (m, 1H), 2.98 (d, J=7.1 Hz, 2H), 3.57 (m, 2H), 7.00 (m, 2H), 7.5–8.00 (m, 10H), 10.66 (s, 1H), 12.80 (broad s, 1H). ESI-MS: m/z 461, 260, 200, 182, 115, 105. Anal. Found C, 53.95; H, 4.65; N, 3.97; S, 18.55.

EXAMPLE 15

Preparation of 3-[[4-(Benzoylamino)phenyl] sulfonyl]-2-[(phenylsulfanyl)methyl]propanoic acid

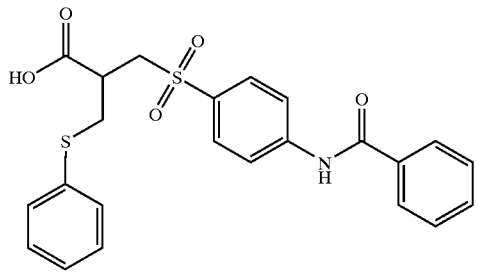

Following the general procedure outlined in Example 14 and making non-critical variations but starting with thiophenol in step 5, the title compound was obtained as a white powder.

$^1$H NMR (400 MHz, DMSO-d$_6$): δ 2.70 (m, 1H), 3.15 (m, 2H), 3.57 (dd, J=4.4 and 14.4 Hz, 1H), 3.63 (dd, J=8.1 and 14.4 Hz, 1H), 7.2–7.6 (m, 8H), 7.8–8.1 (m, 6H), 10.66 (s, 1H), 12.80 (broad s, 1H). ESI-MS: m/z 455, 331, 260, 194, 123, 110, 105, 77. Anal. Found C, 60.03; H, 5.29; N, 3.28; S, 11.68.

EXAMPLE 16

Preparation of 3-[(4'-chloro[1,1'-biphenyl]-4-yl) sulfonyl]-2-[[(4-hydroxyphenyl)sulfanyl]methyl] propanoic acid

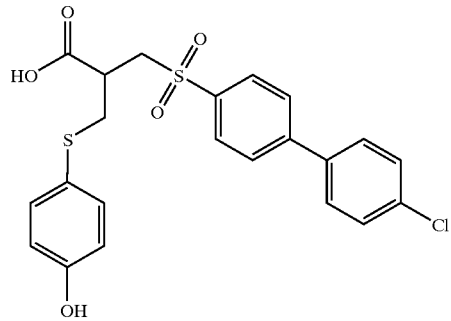

A solution of 2-[(4'-chloro[1,1'-biphenyl]-4-yl)sulfonyl] methyl]acrylic acid (3.4 g) and 4-hydroxythiophenol (3 g) in 20 mL of DMF was heated for 5 h at 60° C. After cooling, the residue was chromatographed on silica gel eluting with CHCl$_3$/cyclohexane 1/2. The fractions containing the product were pooled and the solvent removed. The residue was crystallized from CHCl$_3$/cyclohexane 1/3 affording 2.7 g of the title compound as a white powder.

$^1$H NMR (400 MHz, DMSO-d$_6$): δ 2.58 (m, 1H), 2.95 (m, 2H), 3.64 (m, 2H), 6.63 (d, J=8.5 Hz, 2H), 7.06 (d, J=8.5 Hz, 2H), 7.58 (d, J=8.5 Hz, 2H), 7.79 (d, J=8.5 Hz, 2H), 7.86 (d, J=8.5 Hz, 2H), 7.92 (d, J=8.5 Hz, 2H), 9.60 (broad s, 1H), 12.80 (br s, 1H). MS (EI): m/z 462, 251, 210, 152, 126. Anal. Found C, 56.95; H, 4.25; S, 13.68.

EXAMPLE 17

Preparation of 3-[(4'-Chloro[1,1'-biphenyl]-4-yl) sulfonyl]-2-(phenoxymethyl)propanoic acid, sodium salt

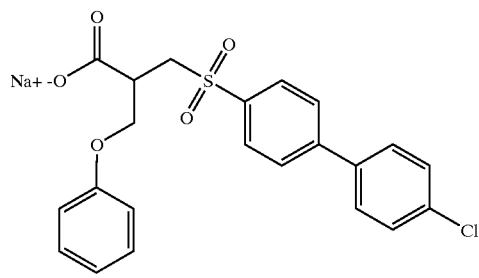

To a stirred solution of a-bromomethylacrylic acid (4.95 g) and NaHCO$_3$ (4 g) in 25 mL of DMF was added phenol (4.5 g) and the resulting suspension was heated at 75° C. for 5 h. After disappearance of α-bromomethylacrylic acid, checked by tlc and HPLC, the solution was cooled at −15° C. and 4'-chloro[1,1'-biphenyl]-4-thiol (9.2 g) was added. After stirring 1 h at room temperature, the solution was diluted with ethyl acetate and washed thoroughly with 0.1 M citric acid. After drying and removal of the solvent, the residue was chromatographed on silica gel eluting with CHCl$_3$/cyclohexane 1/2 to provide 4.9 g of 3-[(4'-Chloro[1, 1'-biphenyl]-4-yl)sulfanyl]-2-phenoxymethyl]propanoic acid as a white foam. A solution of this intermediate (4.6 g) in 50 mL of ethanol was added dropwise to a stirred solution of Oxone® (15 g) in 100 mL of DMF at 45° C. After stirring for 4 h, the solvent was evaporated off and the residue was partitioned between chloroform and water. After drying and removal of the solvent, the crude residue was chromatographed on silica gel eluting with chloroform to provide 3.9 g of 3-[(4'-Chloro[1,1'-biphenyl]-4-yl)sulfonyl]-2-phenoxymethyl]propanoic acid as white foam. To a solution of this intermediate (2.15 g) in 100 mL of EtOH was added 1 M NaOH (6 mL). The resulting solution was charcoalized then filtered. Concentration in vacuum afforded 1.9 g of the title compound as shiny crystals.

$^{1}$H NMR (400 MHz, DMSO-d$_{6}$): δ 2.55 (m, 1H), 3.44 (dd, J=8.3 and 14.6 Hz, 1H), 3.97 (dd, J=3.7 and 14.6 Hz, 1H), 4.01 (dd, J=4.4 and 8.8 Hz, 1H), 4.20 (dd, J=4.4 and 8.8 Hz, 1H), 6.75 (d, J=8.8 Hz, 2H), 6.83 (t, J=7.3 Hz, 1H), 7.18 (dd, J=7.3 and 8.8 Hz, 2H), 7.56 (d, J=8.8 Hz, 2H), 7.72 (d, J=8.8 Hz, 2H), 7.85 (d, J=8.5 Hz, 2H), 7.91 (d, J=8.5 Hz, 2H). ESI(−)-MS: m/z 429, 291, 251. Anal. Found C, 55.54; H, 4.52; S, 6.74.

EXAMPLE 18

Preparation of 3-[(4'-chloro[1,1'-biphenyl]-4-yl)sulfonyl]-2-[(3-butyl-2,4-dioxo-1-imidazolidinyl)methyl]propanoic acid

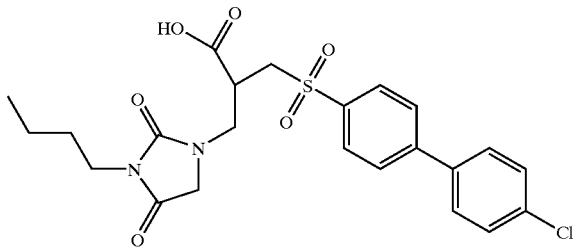

To stirred solution of glycine ethyl ester hydrochloride (6.0 g) and TEA (16 mL) in 80 mL of DMF was added α-bromomethylacrylic acid (5 g) at 0° C. After stirring for 2 h at rt, the suspension was filtered and the filtrate was evaporated to dryness. The residue dissolved in 50 mL of dioxane was treated with n-butyl isocyanide (4 mL) and heated for 5 h at 65° C. The solvent was removed and the crude residue was columned over a small pad of silica gel eluting with dichloromethane to afford 5.5 g of 2-[(3-butyl-2,4-dioxo-1-imidazolidinyl)methyl]acrylic acid as an oil. This intermediate (5.5 g) was dissolved in DMF (50 mL) and treated at 0° C. with 4'-chloro[1,1'-biphenyl]-4-thiol (5.5 g) and NaHCO$_{3}$ (3.9 g). After stirring 1 h at rt, the reaction mixture was concentrated in vacuo, taken up in ethyl acetate and sequentially washed with 0.5 M HCl and brine. After drying over anhydrous sodium sulfate, the solvent was removed and the residue was chromatographed on silica eluting with ethyl acetate/cyclohexane 1/1 to provide 4.6 g of 3-[(4'-chloro[1,1'-biphenyl]-4-yl)sulfanyl]-2-[(3-butyl-2,4-dioxo-1-imidazolidinyl)methyl]propanoic acid. A solution of this intermediate (4.5 g) and Oxone® (13 g) in 100 ml of DMF was heated for 1 h at 50°. The reaction mixture was concentrated in vacuo and the residue was partitioned between ethyl acetate and water. After drying over sodium sulfate, the solvent was removed in vacuo and the residue was columned over a small pad of silica gel eluting with CHCl3 to give the title compound (4.2 g) as a white powder.

$^{1}$H NMR (400 MHz, DMSO-d$_{6}$): δ 0.83 (t, J=7.3 Hz, 3H), 1.20 (m, 2H), 1.40 (m, 2H), 3.00 (m, 1H), 3.30 (m, 2H), 3,52 (d, J=7.6 Hz, 2H), 3,53 (m, 1H), 3.71 (dd, J=8.3 and 14.9 Hz, 1H), 3.79 and 3.93 (two d, J=17.3 Hz, 2H), 7.58 (d, J=8.5 Hz, 2H), 7.79 (d, J=8.5 Hz, 2H), 7.94 (s, 4H), 12.90 (broad s, 1H). ESI(+)-MS: m/z 493, 475, 319, 235, 223. Anal. Found C, 55.38; H, 5.19; N, 5.33; S, 6.78.

EXAMPLE 19

Preparation of 3-[(4'-cyano[1,1'-biphenyl]-4-yl)sulfonyl]-2-[(phenylsulfanyl)methyl]propanoic acid

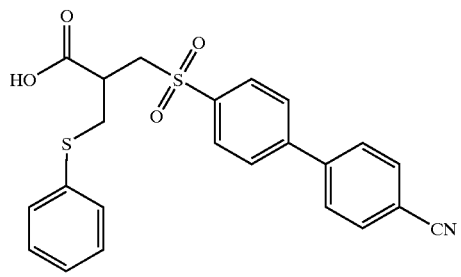

Step 1. 4-Cyano-4'-[[(dimethylamino)carbothioyl]oxy]-1,1'-biphenyl.

Sodium hydride (80% in oil; 4.6 g) was added portionwise to a stirred solution of 4-hydroxy[1,1'-biphenyl]-4'-carbonitrile (26.8 g) in DMF (150 mL) at −10° C. After stirring for 20 min, a solution of dimethylthiocarbamoyl chloride (23 g) in DMF (50 mL) was added dropwise. The resulting mixture was maintained for additional 15 min at −10° C., then heated at 80° C. for 1 h. After cooling, ice water was added. The resulting precipitate was filtered, thoroughly washed with water, then with acetone, to furnish 37 g of the title compound as a white powder, mp 243–247° C.

Step 2. 4-Cyano-4'-[[dimethylamino)carbonyl]sulfanyl]-1,1-biphenyl.

The compound from step 1 above (33 g) was heated at 240° C. under a nitrogen blanket. After melting, the compound was heated for additional 45 min, then cooled to room temperature and dissolved in acetone. Charcoal was added, filtered off, and the solvent removed in vacuo. The residue was crystallized from a small volume of boiling ethanol to obtain 30 g of the title compound, mp 268–270° C.

Step 3. 4'-Cyano[1,1'-biphenyl]-4-thiol.

The compound from step 2 above (31 g) in methanol (1 L) was treated with 1N NaOH (120 mL) and the mixture was refluxed for 5 h. After cooling, 1 N HCl (150 mL) was added, and the mixture was concentrated in vacuo to remove the organic solvent. The crystalline precipitate was filtered, washed with water and then with ethanol, to provide 20 g of the title compound as white crystals, mp. 192–195° C.

Steps 4–6. 3-[(4'-Cyano[1,1'-biphenyl]-4-yl)sulfonyl]-2-[(phenylsulfanyl)methyl]propanoic acid.

By following the procedure described in Example 1, steps 4–6, and making non-critical variations, but replacing 4'-chloro[1,1'-biphenyl])thiol with 4'-cyano[1,1'-biphenyl]-4-thiol, the title compound was obtained as a white powder.

$^{1}$H NMR (400 MHz, DMSO-d$_{6}$): δ 3.09 (m, 2H), 3.36 (m, 1H), 3.61 (dd, J=3.8 and 14.5 Hz, 1H), 3.70 (dd, J=7.7 and 14.5 Hz, 1H), 7.20 (m, 5H), 7.6–7.7 (m, 6H), 7.94 (d, J=8.5 Hz, 2H). Anal. Found C, 62.83; H, 4.41; N, 3.13; S, 14.29.

EXAMPLE 20

Preparation of 3-[(4'-chloro[1,1'-biphenyl]-4-yl)sulfonyl]-2-[(2-pyridinylsulfanyl)methyl]propanoic acid

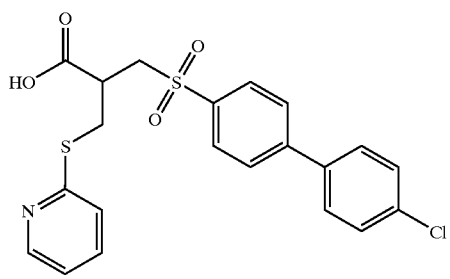

Following the general procedure outlined in Example 16 and making non-critical variations but replacing 4-hydroxythiophenol with 2-mercapropyridine, the title compound was obtained as a white crystalline powder.

$^1$H NMR (300 MHz, DMSO-d$_6$): δ 2.99 (m, 1H), 3.37 (d, J=7.5 Hz, 1H), 3.66 (dd, J=4.1 and 14.6 Hz, 1H), 3.70 (dd, J=8.3 and 14.6 Hz, 1H), 7.01 (ddd, J=1.0, 4.9 and 7.4 Hz, 1H), 7.18 (ddd, J=0.9, 1.0 and 8.1 Hz, 1H), 7.50 (ddd, J=1.9, 7.4 and 8.1 Hz, 1H), 7.56 (d, J=8.6 Hz, 2H), 7.76 (d, J=8.6 Hz, 2H), 7.88 (m, 4H), 8.30 (ddd, J=0.9, 1.9 and 4.9 Hz, 1H), 12.85 (broad s, 1H). ESI(+)-MS: m/z 448, 319, 235, 178. Anal. Found C, 56.26: H, 4.09; N, 3.17; S, 14.30.

EXAMPLE 21

Preparation of 3-[[4-[(4-chlorobenzoyl)amino]phenyl]sulfonyl]-2-[(phenylsulfanyl)methyl]propanoic acid

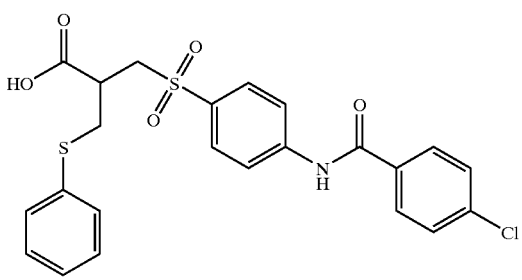

Following the general procedure outlined in Example 14 and making non-critical variations but starting with 4-chlorobenzoyl chloride in step 1, and replacing 2-thiophenethiol with thiophenol in step 5, the title compound was obtained as a white powder.

$^1$H NMR (400 MHz, DMSO-d$_6$): δ 2.67 (m, 1H), 3.15 (m, 2H), 3.62 (m, 2H), 7.22 (m, 5H), 7.64 (d, J=8.5 Hz, 2H), 7.77 (d, J=8.0 Hz, 2H), 8.01 (m, 4H), 10.70 (s, 1H), 12.80 (broad s, 1H). ESI(-)-MS: m/z 510 [M+Na-2H]$^-$, 334. Anal. Found C, 55.66; H, 4.10; N, 2.91; S, 12.82.

EXAMPLE 22

Preparation of 3-[(4'-chloro[1,1'-biphenyl]-4-yl)sulfonyl]-2-[(2-pyrimidinylsulfanyl)methyl]propanoic acid

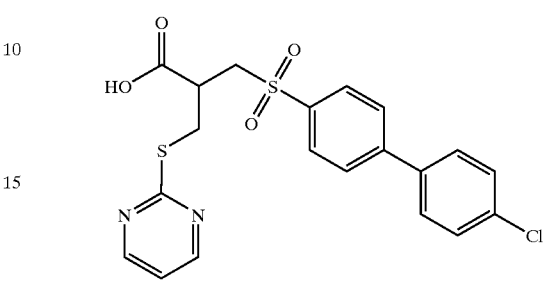

Step 1. 3-Bromo-2-[(4'-chloro[1,1'-biphenyl]-4-yl)sulfonyl]methyl]propanoic acid.

2-[[(4'-Chloro[1,1'-biphenyl]-4-yl)sulfonyl]methyl] acrylic acid (4 g), prepared as described in Example 1, step 5, was suspended in 33% HBr in acetic acid (40 mL). After stirring for 4 h at ambient temperature, the reaction mixture was concentrated in vacuo, taken up in toluene and evapoared to dryness (twice). The residue was triturated with ethyl is ether, whereby the title product separated as a white crystalline powder, which was collected by filtration (3.85 g). A second crop (0.3 g) was recovered from the mother liquors by repeating the process after evaporation to dryness.

Step 2. 3-[(4'-Chloro[1,1'-biphenyl]-4-yl)sulfonyl]-2-[(2-pyrimidinylsulfanyl)methyl]propanoic acid.

2-Mercapropyrimidine (3.65 g) was added portionwise to a suspension of sodium hydride (60% dispersion in mineral oil; 1.21 g) in anhydrous DMF (80 mL) under an argon blanket, and the mixture stirred for 20 min at room temperature to obtain a clear solution, after which time the bromomethylpropanoic acid from step 1 above (4.54 g) was added. After 4 h at room temperature, 0.2 N HCl (600 mL) was added, and the mixture was extracted twice with ethyl acetate. The organic extract was washed with brine, dried over sodium sulfate, evaporated, taken up in toluene and evaporated again to dryness. Trituration of the residue with ethyl ether afforded a powder (2.99 g), which was purified by stirring for 1 h in a mixture of ether/ethyl acetate 9/1 and filtration, thereby obtaining the title product (2.7 g) as a white powder, mp 166–168° C.

$^1$H NMR (300 MHz, DMSO-d$_6$): δ 3.06 (m, 1H), 3.28 (partially overlapped by 5 water, 2H), 3.62 (dd, J=4.0 and 14.6 Hz, 1H), 3.72 (dd, J=8.2 and 14.6 Hz, 1H), 7.10 (t, J=4.9 Hz, 1H), 7.57 (d, J=8.5 Hz, 2H), 7.75 (d, J=8.5 Hz, 2H), 7.90 (m, 4H), 8.50 (d, J=4.9 Hz, 2H), 13.00 (broad s, 1H). ESI(+)-MS: m/z 449, 319,235, 179, 113. Anal. Found C, 53.65; H, 3.92; N, 6.21; S, 14.30.

EXAMPLE 23

Preparation of 3-[(4'-chloro[1,1'-biphenyl]-4-yl)sulfonyl]-2-[[(5-amino-1,3,4-thiadiazol-2-yl)sulfanyl]methyl]propanoic acid

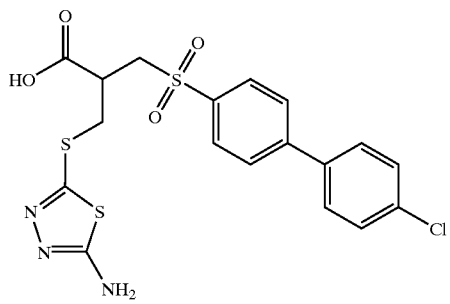

Following the general procedure outlined in Example 22 and making non-critical variations but replacing 2-mercapropyrimidine with 5-amino-2-mercapto-1,3,4-thiadiazole, the title compound was obtained as a yellowish powder, mp 184–186° C.

$^1$H NMR (400 MHz, DMSO-d$_6$): δ 2.98 (m, 1H), 3.30 (m, 2H), 3.68 (m, 2H), 7.33 (s, 2H), 7.57 (d, J=8.5 Hz, 2H), 7.78 (d, .J=8.5 Hz, 2H), 7.92 (m, 4H), 13.00 (broad s, 1H). ESI(+)-MS: m/z 470, 337, 319, 235. Anal. Found C, 41.38; H, 3.42; N, 10.83; S, 22.89.

EXAMPLE 24

Preparation of 3-[(4'chloro[1,1'-biphenyl]-4-yl)sulfonyl]-2-[(2-methyl-2H-1,2,3-triazol-4-yl)sulfanyl]methyl]propanoic acid

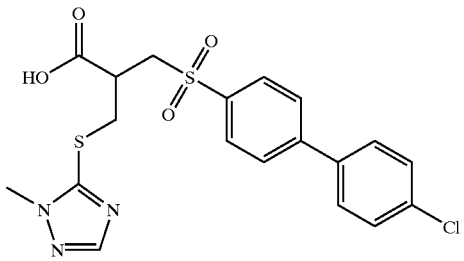

Following the general procedure outlined in Example 22 and making non-critical variations but replacing 2-mercapropyrimidine with 4-mercapto-2-methyl-2H-1,2,3-triazole, the title compound was obtained as a white powder, mp 166–168° C.

$^1$H NMR (400 MHz, DMSO-d$_6$): δ 3.02 (m, 1H), 3.34 (m, 2H), 3.48 (m, 3H), 3.69 (m, 2H), 7.58 (d, J=8.5 Hz, 2H), 7.79 (d, J=8.5 Hz, 2H), 7.91 (m, 4H), 8.49 (s, 1H), 12.98 (broad s, 1H). ESI(+)-MS: m/z 452, 337, 319, 235. Anal. Found C, 50.18; H, 4.06; N, 9.25; S, 13.45.

EXAMPLE 25

Preparation of 3-[(4'-chloro[1,1'-biphenyl]-4-yl)sulfonyl]-2-[[(1-methyl-1H-imidazol-2-yl)sulfanyl]methyl]propanoic acid

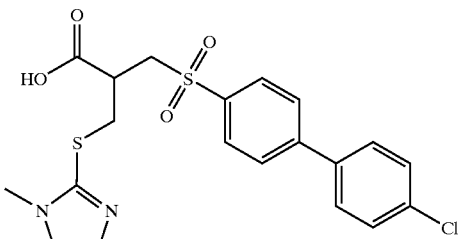

Following the general procedure outlined in Example 22 and making non-critical variations but replacing 2-mercapropyrimidine with 2-mercapto-1-methyl-1H-imidazole, the title compound was obtained as a whitish powder.

$^1$H NMR (400 MHz, DMSO-d$_6$): δ 2.90 (m, 1H), 3.20 (m, 2H), 3.63 (m, 2H), 6.88 (d, J=2.1 Hz, 1H), 7.16 (d, J=2.1 Hz, 1H), 7.56 (d, J=8.5 Hz, 2H), 7.78 (d, J=8.5 Hz, 2H), 7.91 (m, 4H). ESI(+)-MS: m/z 451, 337, 235, 199, 181.

EXAMPLE 26

Preparation of 3-[(4'-chloro[1,1'-biphenyl]-4-yl)sulfonyl]-2-[[(2,6-dimethyl-4-pyrimidinyl)sulfanyl]methyl]propanoic acid

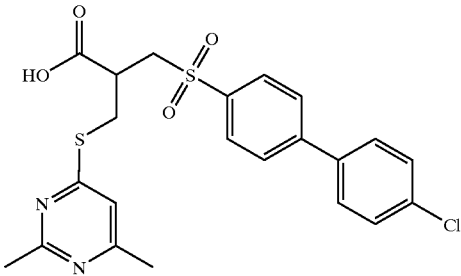

Following the general procedure outlined in Example 22 and making non-critical variations but replacing 2-mercapropyrimidine with 2,6-dimethyl-4-mercapropyrimidine, the title compound was obtained as a white powder, mp 170–172° C.

ESI(+)-MS: m/z 477, 336, 251, 187, 152, 140. Anal. Found C, 55.05; H, 4.52; N, 4.64; S, 12.32.

EXAMPLE 27

Preparation of 3-[(4'-chloro[1,1'-biphenyl]-4-yl)sulfonyl]-2-[[(4,6-dimethyl-2-pyrimidinyl)sulfanyl]methyl]propanoic acid

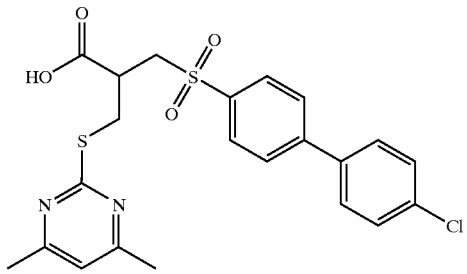

Following the general procedure outlined in Example 22 and making non-critical variations but replacing 2-mercapropyrimidine with 4,6-dimethyl-2-mercapropyrimidine, the title compound was obtained as a white powder, mp 170–172° C.

$^1$H NMR (400 MHz, DMSO-$d_6$): δ 2.20 (s, 6H), 3.05 (m, 1H), 330 (m, 2H), 3.61 (dd, J=3.4 and 14.5 Hz, 1H), 3.73 (d, J=8.1 and 14.5 Hz, 1H), 6.81 (s, 1H), 7.58 (d, J=8.5 Hz, 2H), 7.75 (d, J=8.5 Hz, 2H), 7.88 (m, 4H), 12.90 (broad s, 1H). ESI(+)-MS: m/z 477, 319, 294, 235, 225, 141. Anal. Found C, 53.90; H, 4.52; N, 5.70; S, 12.48.

EXAMPLE 28

Preparation of 3-[(4'-chloro[1,1'-biphenyl]-4-yl)sulfonyl]-2-[(1,3-thiazol-2-ylsulfanyl)methyl]propanoic acid

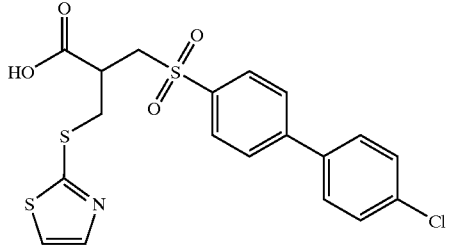

Following the general procedure outlined in Example 22 and making non-critical variations but replacing 2-mercapropyrimidine with 2-mercaptothiazole, the title compound was obtained as a white powder, mp 152–154° C.

$^1$H NMR (400 MHz, DMSO-$d_6$): δ 3.00 (m, 114), 3.45 (m, 2H), 3.63 (dd, J=4.7 and 14.5 Hz, 1H), 3.74 (d, J=7.7 and 14.5 Hz, 1H), 7.57 (m, 3H), 7.65 (d, J=3.4 Hz, 1H), 7.60 (d, J=8.5 Hz, 2H), 7.77 (d, J=8.5 Hz, 2H), 7.91 (m, 4H), 13.00 (broad s, 1H). ESI(+)-MS: m/z 454, 337, 319, 294, 235, 184. Anal. Found C, 50.07; H, 3.69; N, 3.15; S, 21.14.

EXAMPLE 29

Preparation of 3-[(4'-cyano[1,1'-biphenyl]-4-yl)sulfonyl]-2-(phenoxymethyl)propanoic acid, sodium salt

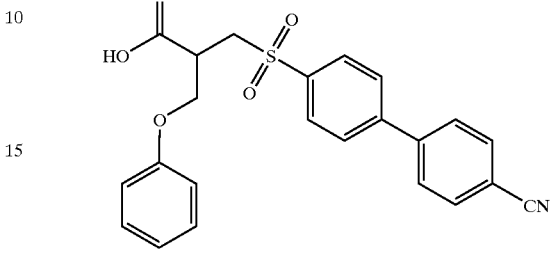

Following the general procedure outlined in Example 17 and making non-critical variations but replacing 4'-chloro[1,1'-biphenyl]-4-thiol with 4'-cyano[1,1'-biphenyl]-4-thiol, the title compound was obtained as a white powder.

Anal. Found C, 59.59, H, 4.45; N, 2.88; S, 6.85.

EXAMPLE 30

Preparation of 3-[(4'-chloro[1,1'-biphenyl]-4-yl)sulfonyl]-2-[(4-acetylaminophenoxy)methyl]propanoic acid

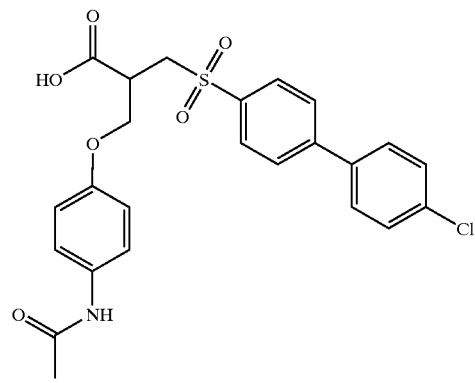

Following the general procedure outlined in Example 17 and making non-critical variations but replacing phenol with 4-acetamidophenol, the title compound was obtained as a white powder.

Anal. Found C, 58.03; H, 4.61; N, 2.75; S, 6.84.

EXAMPLE 31

Preparation of 3-[(4'-chloro[1,1'-biphenyl]-4-yl)sulfonyl]-2-[[(4-hydroxy-6-methyl-2-pyrimidinyl)sulfanyl]methyl]propanoic acid

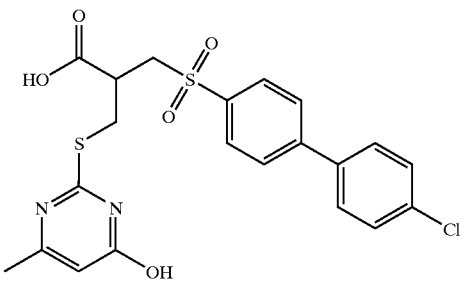

Following the general procedure outlined in Example 22 and making non-critical variations but replacing 2-mercapropylimidine with 4-hydroxy-6-methyl-2-mercaptopyrimidine, the title compound was obtained as a white powder, mp 165–168° C.

EXAMPLE 32

Preparation of 3-[(4'-chloro[1,1'-biphenyl]-4-yl)sulfonyl]-2-[[(1-methyl-1H-tetrazol-5-yl)sulfanyl]methyl]propanoic acid

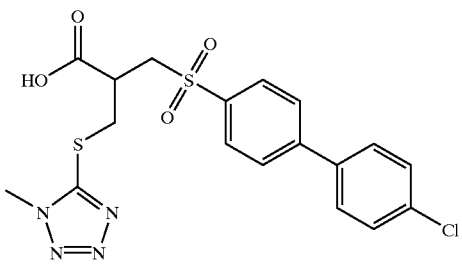

Following the general procedure outlined in Example 22 and making non-critical variations but replacing 2-mercapropyrimidine with 1-methyl-1H-tetrazole-5-thiol, the title compound was obtained as a whitish powder, mp 98–100° C.

$^1$H NMR (500 MHz, DMSO-$d_6$): δ 3.08 (m, 1H), 3.54 (m, 2H), 3.70 (dd, J=4.3 and 14.6 Hz, 1H), 3.76 (dd, J=7.6 and 14.6 Hz, 1H), 3.85 (s, 3H), 7.59 (d, J=8.5 Hz, 2H), 7.79 (d, J=8.5 Hz, 2H), 7.92 (m, 4H), 13.00 (broad s, 1H). ESI(+)-MS: m/z 453, 337, 319, 294, 235. Anal. Found C, 47.64; H, 4.59; N, 13.18; S, 11.86.

EXAMPLE 33

Preparation of 3-[(4'-chloro[1,1'-biphenyl]-4-yl)sulfonyl]-2-[[2-(hydroxymethyl)phenoxy]-methyl]propanoic acid

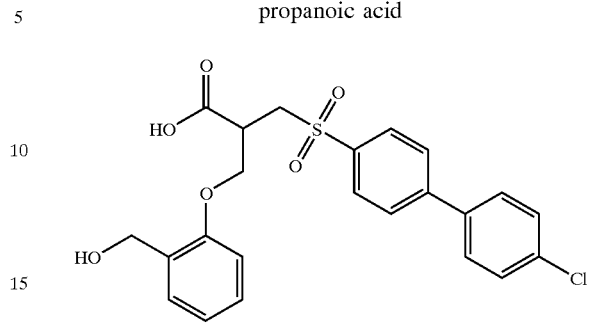

Following the general procedure outlined in Example 17 and making non-critical variations but replacing phenol with salicyl alcohol, the title compound was obtained as a crystalline powder.

Anal. Found C, 59.50; H, 4.62; S, 6.98.

EXAMPLE 34

Preparation of 3-[[4-[(4-chlorobenzoyl)amino]phenyl]sulfonyl]-2-(phenoxymethyl)propanoic acid

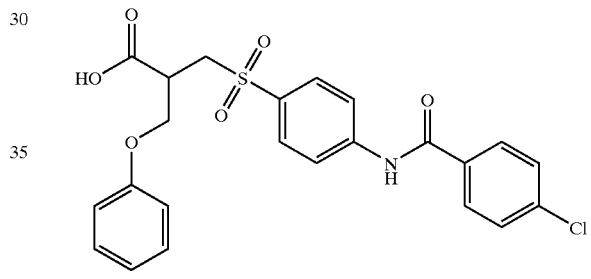

Following the general procedure outlined in Example 17 and making non-critical variations but replacing 4-chloro[1,1'-biphenyl]-4-thiol with 4-chloro-N-(4-sulfanyl)benzamide, the title compound was obtained as a white powder.

Anal. Found C, 57.72; H, 4.28; N, 3.02; S, 6.62.

EXAMPLE 35

Preparation of 3-[[4-[(4-cyanobenzoyl)amino]phenyl]sulfonyl]-2-(phenoxymethyl)propanoic acid

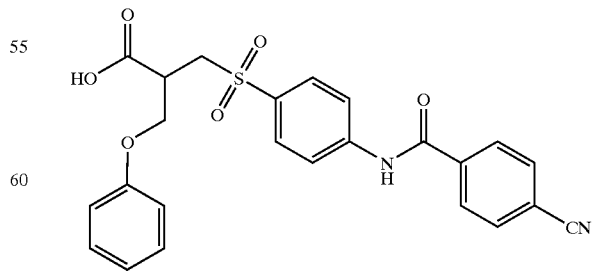

Following the general procedure outlined in Example 17 and making non-critical variations but replacing 4-chloro[1, 1'-biphenyl]-4-thiol with 4-cyano-N-(4-sulfanyl)benzamide, the title compound was obtained as a white powder.

Anal. Found C, 61.33; H, 4.26; N, 6.19; S, 7.15.

EXAMPLE 36

Preparation of 3-[(4'-chloro[1,1'-biphenyl]-4-yl)sulfonyl]-2-[[(S-methyl-1,3,4-thiadiazol-2-yl)sulfanyl]methyl]propanoic acid.

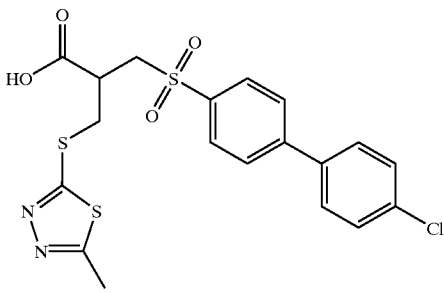

Following the general procedure outlined in Example 22 and making non-critical variations but replacing 2-mercapropyrimidine with 5-methyl-2-mercapto-1,3,4-thiadiazole, the title compound was obtained as a whitish powder, mp 147–150° C.

Anal. Found C, 47.03; H, 3.74; N, 5.69; S, 18.73.

EXAMPLE 37

Preparation of 3-[(4'-chloro[1,1'-biphenyl]-4-yl)sulfonyl]-2-[(1H-benzimidazol-2-yl-sulfanyl)methyl]-propanoic acid

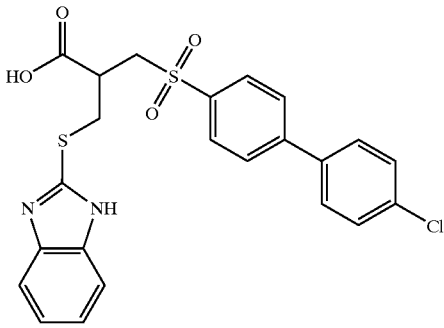

Following the general procedure outlined in Example 22 and making non-critical variations but replacing 2-mercarpropyrimidine with 2-mercapto-1H-benzimidazole, the title compound was obtained as a whitish powder, mp 176–179° C.

Anal. Found C, 55.43; H, 3.96; N, 5.57; S, 12.32.

EXAMPLE 38

Biochemical Activity Test

The inhibitory activity of the compounds of the present invention was evaluated in vitro against one or more of the MMP enzymes (gelatinases, collagenases, stromelysins) using the internal fluorescence quenching method. The assay method is based on the hydrolysis of the MMP substrate, MCA-Pro-Leu-Gly-Leu-DPA-Ala—Arg-NH$_2$ at 37° C. (see Knight, C. G. et al., FEBS Lett. 296:263–266, 1992). The enzymes cleave at the Gly-Leu bond removing the internally quenching DPA group. The release of the highly fluorescent peptide MCA-Pro-Leu was monitored with a LS50 Perkin Elmer fluorimeter equipped with a Peltier-thermostated cell holder using an excitation wavelength of 326 nm and an emission wavelenght of 398 nm. Slis were set at 14/14. Proper determination of steady-state rates of substrate cleavage required a preincubation at 37° C. of 15 minutes to allow for complete equilibration of the enzyme-inhibitor complex. For the determination of the apparent Ki (Ki$_{app}$), the concentration of the inhibitor was varied at a constant and low concentration of the substrate (3 μM). Rates of substrate hydrolysis, expressed as fluorescence arbitrary units per minute, were calculated by least-square analysis of the steady-state linear progression curves. The steady-state rates were fitted to the Michaelis equation describing competitive inhibition; in particular, Ki$_{app}$ were determined by fining the data to the tight-binding equation of Morrison (Biochem. Biophys. Acta, 185:269–286, 1969) by non-linear methods. Since the Michaelis constants (K$_m$) for the MCA peptide substrate with the MMPs is quite high (70 μM or greater; see Knight, C. G. et al., reference above) and by far exceeds the substrate concentration, the factor (1+S/K$_m$) can be approximated to unity without appreciable error, so that the determined Ki$_{app}$ will be essentially equal to Ki.

Human gelatinase-A (MMP-2) was obtained as penzyme (72 kDa) and was activated with 1 mM 4-aminophenylmercuric acetate for 30 min at 37° C. immediately prior to use. The inhibitor was diluted into the assay from a stock solution in 100% DMSO, and controls substituted an equal volume of DMSO so that the final DMSO concentration from inhibitor and substrate dilution in all assays was 1%. The concentration of MMP-2 was 19.2 picoM. For compounds of formula (I) where X is —OH, the assay buffer was 50 mM Tris/HCl pH 6.5 containing 150 mM NaCl, 10 mM CaCl$_2$, 0.01 mM ZnCl$_2$ and 0.05% Brij35 (Protocol A). Other conditions were as stated above.

Human fibroblast collagenase (MMP-1) was obtained as truncated recombinant enzyme encompassing residues 101–269 and did not require activation. Assay conditions were the same as above, but enzyme concentration was 200 picoM.

Inhibitory data (Ki's against MMP-2 and MMP-1, all nanoM; Protocol A) for some representative compounds of formula (I) wherein X is H are displayed in Table 1.

TABLE 1

| Example No. | MMP-2 Ki (nanoM) | MMP-1 Ki (nanoM) |
| --- | --- | --- |
| 1 | 8.3 | >2500 |
| 3, Isomer 1 | 6.0 | 6600 |
| 3, Isomer 2 | 660 | 33190 |
| 5 | 5.5 | >2000 |
| 6, Isomer 1 | 3.7 | 3600 |
| 6, Isomer 2 | 50 | n.t. |
| 7 | 42 | n.t. |
| 9 | 3 | n.t. |
| 11 | 4 | n.t. |
| 13 | 12 | 5286 |
| 14 | 8 | n.t. |
| 15 | 7 | 81090 |
| 16 | 9 | 9697 |
| 17 | 9.2 | 14740 |
| 18 | 7.8 | n.t. |
| 19 | 17 | n.t. |
| 20 | 3.9 | 6291 |
| 21 | 1.4 | 50560 |

TABLE 1-continued

| Example No. | MMP-2 Ki (nanoM) | MMP-1 Ki (nanoM) |
|---|---|---|
| 22 | 8 | 8033 |
| 23 | 25 | n.t. |
| 24 | 24 | n.t. |
| 25 | 16 | n.t. |
| 26 | 26.8 | n.t. |
| 27 | 22.8 | n.t. |
| 28 | 6.6 | n.t. |
| 29 | 21.5 | n.t. |
| 30 | 46 | 19580 |
| 32 | 26 | n.t. |
| 33 | 15 | n.t. |
| 34 | 2.4 | 53980 |
| 35 | 4.8 | 67520 |
| 36 | 33.4 | n.t. |
| 37 | 18.2 | n.t. |

The compounds of formula (I) where X is —NHOH were tested against MMP-2 and MMP-1 under the conditions stated above, but the assay solution was buffered at pH 7.4 (Protocol B). Inhibitory data (Ki's, all picoM) for some representative compounds of formula (I) wherein X is —NHOH are displayed in Table 2.

TABLE 2

| Example No. | MMP-2 Ki (picoM) | MMP-1 Ki (picoM) |
|---|---|---|
| 4 | 159 | 149000 |
| 8 | 107 | 26800 |
| 10 | 50 | 12600 |
| 12 | 69 | 17100 |

What is claimed is:

1. A compound which is a 3-arylsulfonyl-2-methyl propanoic acid derivative of formula (I):

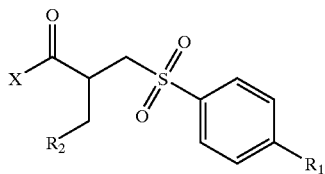

(I)

wherein

X is HO—NH— or HO—;

$R_1$ is selected from the group consisting of phenyl, 4-chlorophenyl, 4-fluorophenyl, 4-cyanophenyl, benzamido and benzamido substituted on the terminal phenyl ring by $C_1$–$C_4$ alkyl, fluoro, chloro, cyano or $C_1$–$C_4$ alkoxy;

$R_2$ is selected from:
2,5-dioxo-1-imidazolidinyl or 2,4-dioxo-1-imidazolidinyl, which may be optionally substituted at the carbon atom by one or two methyl, linear or branched $C_2$–$C_4$ alkyl, phenyl, benzyl or hydroxymethyl groups, and at the nitrogen atom with $C_1$–$C_4$ linear or branched alkyl;

or a pharmaceutically acceptable salt thereof.

2. A compound according to claim 1 which is an isomer having the configuration depicted in formula (I'):

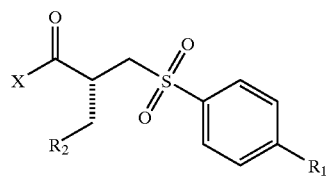

(I')

wherein X, $R_1$ and $R_2$ are as defined in claim 1.

3. A compound according to claim 1 which is selected from:

3-[(1,1'-Biphenyl]-4-ylsulfaonyl)-2-[(3,4,4-trimethyl-2,5-dioxo-1-imidazolidinyl)methyl]propanoic acid;

3-[(4'-Chloro[1,1'-biphenyl]-4-yl)sulfonyl]-2-[(3,4,4-trimethyl-2,5-dioxo-1-imidazolidinyl)methyl]propanoic acid;

(2R)-3-[(4'-Chloro[1,1'-biphenyl]-4-yl)sulfonyl]-2-[(3,4,4-trimethyl-2,5-dioxo-1-imidazolidinyl)methyl]propanoic acid;

3-[(4'-Chloro[1,1'-biphenyl]-4-yl)sulfonyl]-N-hydroxy-2-[(3,4,4-trimethyl-2,5-dioxo-1-imidazolidinyl)methyl]propanamide;

3-[(4'-Chloro[1,1'-biphenyl]-4-yl)sulfonyl]-2-[(4,4-dimethyl-2,5-dioxo-1-imidazolidinyl)methyl]propanoic acid;

3-[(4'-Chloro[1,1'-biphenyl]-4-yl)sulfonyl]-N-hydroxy-2-[(4,4-dimethyl-2,5-dioxo-1-imidazolidinyl)methyl]propanamide;

3-[(4'-Chloro[1,1'-biphenyl]-4-yl)sulfonyl]-2-[(2,5-dioxo-1-imidazolidinyl)methyl]propanoic acid;

3-[(4'-Chloro[1,1'-biphenyl]-4-yl)sulfonyl]-N-hydroxy-2-[(2,5-dioxo-1-imidazolidinyl)-methyl]propanamide;

3-[(4'-Chloro[1,1'-biphenyl]-4-yl)sulfonyl]-2-[(3-methyl-2,5-dioxo-1-imidazolidinyl)methyl]propanoic acid;

3-[(4'-Chloro[1,1'-biphenyl]-4-yl)sulfonyl]-2-[(3-ethyl-2,5-dioxo-1-imidazolidinyl)methyl]-propanoic acid;

3-[(4'-Chloro[1,1'-biphenyl]-4-yl)sulfonyl]-2-[(3-butyl-2,5-dioxo-1-imidazolidinyl)methyl]propanoic acid;

3-[(4'-Chloro[1,1'-biphenyl]-4-yl)sulfonyl]-N-hydroxy-2-[(3-butyl-2,5-dioxo-1-imidazolidinyl)methyl]propanamide;

3-[(4'-Chloro[1,1'-biphenyl]-4-yl)sulfonyl]-2-[(3-butyl-2,4-dioxo-1-imidazolidinyl)methyl]propanoic acid;

3-[(4'-Chloro[1,1'-biphenyl]-4-yl)sulfonyl]-N-hydroxy-2-[(3-butyl-2,4-dioxo-1-imidazolidinyl)methyl]propanamide;

3-[(4'-Chloro[1,1'-biphenyl]-4-yl)sulfonyl]-2-[(5-isopropyl-2,4-dioxo-1-imidazolidinyl)methyl]propanoic acid;

3-[(4'-Chloro[1,1'-biphenyl]-4-yl)sulfonyl]-2-[(5-hydroxymethyl-2,4-dioxo-1-imidazolidinyl)methyl]propanoic acid;

3-[(4'-Chloro[1,1'-biphenyl]-4-yl)sulfonyl]-2-[(5-hydroxymethyl-3-methyl-2,4-dioxo-1-imidazolidinyl)methyl]propanoic acid;

3-[(4'-Cyano[1,1'-biphenyl]-4-yl)sulfonyl]-2-[(3-butyl-2,5-dioxo-1-imidazolidinyl)methyl]propanoic acid;

3-[(4'-Chloro[1,1'-biphenyl]-4-yl)sulfonyl]-N-hydroxy-2-[(3-butyl-2,5-dioxo-1-imidazolidinyl)methyl]propanamide;

3-[(4'-Chloro[1,1'-biphenyl]-4-yl)sulfonyl]-2-[(5-hydroxymethyl-2,4-dioxo-1-imidazolidinyl)methyl]propanoic acid;

3-[[4-[(4-Chlorobenzoyl)amino]phenyl]sulfonyl]-2-[(5-hydroxymethyl-2,4-dioxo-1-imidazolidinyl)methyl]propanoic acid;

the pharmaceutically acceptable salts thereof.

4. A process for producing a compound as defined in claim 1, starting from a compound of formula 4:

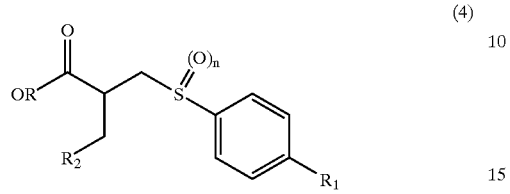

(4)

wherein R is H or the residue of a carboxylic acid ester, $R_1$ is selected from the group consisting of phenyl, 4-chlorophenyl, 4-fluorophenyl, 4-cyanophenyl, benzamido and benzamido substituted on the terminal phenyl ring by $C_1$–$C_4$ alkyl, fluoro, chloro, cyano or $C_1$–$C_4$ alkoxy;

$R_2$ is selected from:
2,5-dioxo-1-imidazolidinyl or 2,4-dioxo-1-imidazolidinyl, which may be optionally substituted at the carbon atom by one or two methyl, linear or branched $C_2$–$C_4$ alkyl, phenyl, benzyl or hydroxymethyl groups, and at the nitrogen atom with $C_1$–$C_4$ linear or branched alkyl; and n is 0 or 2, said process comprising:
(A) hydrolysing a said compound of formula 4 in which R is the residue of a carboxylic and ester to give a compound of formula (I) in which X is HO—; or
(B) hydrolysing and oxidising, in either order, a said compound of formula 4 in which n is 0 and R is the residue of a carboxylic acid ester, to give a compound of formula (I) in which X is HO—; or
(C) activating a said compound of formula 4 wherein R is H and n is 2 to form an activated carboxy group, coupling the activated carboxy group with hydroxylamine or an O-protected derivative thereof and, if necessary, deprotecting the hydroxamic group to give a compound of formula (I) wherein X is —NHOH; or
(D) submitting a said compound of formula 4 wherein R is H and n is zero to a sequence of reactions comprising oxidation at the sulphur atom, activation of the carboxy group, condensation of the activated carboxy group with hydroxylamine or an O-protected derivative thereof and, if necessary, deprotection of the hydroxamic group to form a compound of formula (I) wherein X is —NHOH, the oxidation step being conducted either before the activation step or after the condensation step; and/or
(E) if desired, converting a resulting compound of formula (I) into another compound of formula (I); and/or converting a free compound into a pharmaceutically acceptable salt thereof; and/or converting a salt into a free compound.

5. A process according to claim 4 wherein the compound of formula 4 is obtained by (a) subjecting a compound of formula 2:

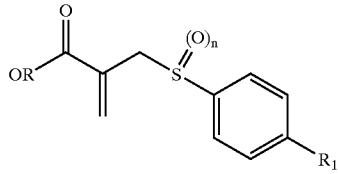

(2)

wherein R is H or the residue of a carboxylic acid ester, $R_1$ is selected from the group consisting of phenyl, 4-chlorophenyl, 4-fluorophenyl, 4-cyanophenyl, benzamido and benzamido substituted on the terminal phenyl ring by $C_1$–$C_4$ alkyl, fluoro, chloro, cyano or $C_1$–$C_4$ alkoxy; and n is 0 or 2 to conjugate addition by treatment with a compound of formula $R_2H$ wherein $R_2$ is selected from:
2,5-dioxo-1-imidazolidinyl or 2,4-dioxo-1-imidazolidinyl, which may be optionally substituted at the carbon atom by one or two methyl, linear or branched $C_2$–$C_4$ alkyl, phenyl, benzyl or hydroxymethyl groups, and at the nitrogen atom with $C_1$–$C_4$ linear or branched alkyl;

(b) treating a compound of formula 3:

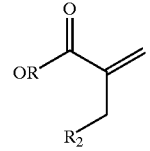

(3)

wherein R and $R_2$ are as defined as above, with a thiol of formula:

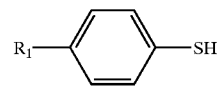

to obtain a compound of formula 4 in which n is zero.

6. A pharmaceutical composition which comprises a pharmaceutically acceptable carrier or diluent and, as an active principle, the compound as defined in claim 1.

7. A method of treating a mammal, including a human, comprising administering the compound claimed in claim 1, to said mammal, including a human, in need thereof.

8. A method for treating a disease in a mammal, including a human, comprising administering an effective amount of the compound as claimed in claim 1, to said mammal, including a human, in need thereof, wherein said disease is a disease mediated by a matrix metalloproteinase.

9. The method as claimed in claim 8, wherein the matrix metalloproteinase is selected from the group consisting of gelatinase (MMP-2), a membrane MMP involved in gelatinase activation (MMP-14), a stromelysin (MMP-3 or MMP-10), collagenase (MMP-13) and neutrophyl collagenase (MMP-8).

10. A method for the prevention of a disease in a mammal, including a human, comprising administering the compound claimed in claim 1, to said mammal, including a human, in need thereof, wherein said disease is a disease mediated by a matrix metalloproteinase.

11. The method as claimed in claim 10, wherein the matrix metalloproteinase is selected from the group consisting of gelatinase (MMP-2), a membrane MMP involved in gelatinase activation (MMP-14), a stromelysin (MMP-3 or MMP-10), collagenase (MMP-13) and neutrophyl collagenase (MMP-8).

12. The method as claimed in claim 8, wherein the disease is selected from the group consisting of tumor growth, tumor metastasis, rheumatoid arthritis, oseoarthritis, ophthalmic disease, cardiovascular disease, periodontal disease, multiple sclerosis and Alzheimer's disease.

13. The method as claimed in claim 12, wherein the disease is selected from the group consisting of tumor growth, tumor metastasis, rheumatoid arthritis, oseoarthritis, ophthalmic disease, cardiovascular disease, periodontal disease, multiple sclerosis and Alzheimer's disease.

* * * * *